(12) United States Patent
Suh et al.

(10) Patent No.: US 10,620,176 B2
(45) Date of Patent: Apr. 14, 2020

(54) LIGHT CONTROLLING ASSEMBLY FOR AN EGG IDENTIFICATION SYSTEM, AND ASSOCIATED METHOD

(71) Applicant: Zoetis Services LLC, Parsippany, NJ (US)

(72) Inventors: William Dongwook Suh, Cary, NC (US); Joel James Walukas, Cary, NC (US)

(73) Assignee: Zoetis Services LLC, Parsippany, NJ (US)

( * ) Notice: Subject to any disclaimer, the term of this patent is extended or adjusted under 35 U.S.C. 154(b) by 0 days.

(21) Appl. No.: 15/841,793

(22) Filed: Dec. 14, 2017

(65) Prior Publication Data

US 2018/0172657 A1 Jun. 21, 2018

Related U.S. Application Data

(60) Provisional application No. 62/436,502, filed on Dec. 20, 2016.

(51) Int. Cl.
| | | |
|---|---|---|
| A01K 43/00 | (2006.01) | |
| G01N 21/59 | (2006.01) | |
| G01N 33/08 | (2006.01) | |

(52) U.S. Cl.
CPC .......... *G01N 33/085* (2013.01); *A01K 43/00* (2013.01); *G01N 21/59* (2013.01)

(58) Field of Classification Search
CPC ....... G01N 33/085; G01N 21/59; A01K 43/00
See application file for complete search history.

(56) References Cited

U.S. PATENT DOCUMENTS

| 4,721,657 A * | 1/1988 | Takahashi ............... C30B 33/00 |
| | | 428/689 |
| 6,234,320 B1 * | 5/2001 | Hebrank ................. A01K 43/00 |
| | | 209/51 |

(Continued)

FOREIGN PATENT DOCUMENTS

| JP | H09 127096 | 5/1997 |
| WO | WO 2015/073939 A1 | 5/2015 |
| WO | WO 2015/074008 A1 | 5/2015 |

OTHER PUBLICATIONS

Outram, B., 2009, Black Coatings to Reduce Stray Light, OPTI 521—Optomechanical Engineering, URL:http://wp.optics.arizona.edu/optomech/student reports/tutorials/2009/Black Coating to Reduce Stray Light.pdf.

(Continued)

*Primary Examiner* — Maurice C Smith
(74) *Attorney, Agent, or Firm* — Scott C. Mayhew

(57) ABSTRACT

An egg identification system for determining viability of an avian egg is provided. Such a system includes an emitter assembly configured to emit electromagnetic radiation having a predetermined wavelength toward an egg. A detector assembly is spaced-apart from the emitter assembly and configured to detect electromagnetic radiation transmitted through the egg. A light controlling assembly is positioned proximate to the emitter assembly. The light controlling assembly includes an absorbing layer configured to absorb electromagnetic radiation at the predetermined wavelength. The absorbing layer defines an opening through which electromagnetic radiation emitted from the emitter assembly is capable of passing therethrough toward the egg. A processor is configured to process an output signal of the detector assembly to determine viability of the egg. An associated method is also provided.

12 Claims, 19 Drawing Sheets

(56) References Cited

U.S. PATENT DOCUMENTS

| | | | | |
|---|---|---|---|---|
| 2005/0057830 A1* | 3/2005 | Coburn, Jr. | ............... | G02B 5/22 |
| | | | | 359/885 |
| 2005/0206876 A1* | 9/2005 | Reeves | ................ | A01K 43/00 |
| | | | | 356/52 |
| 2015/0136988 A1* | 5/2015 | Walukas | ................ | G01N 21/59 |
| | | | | 250/341.1 |
| 2016/0216138 A1* | 7/2016 | Rudmann | ............... | G02B 5/223 |

OTHER PUBLICATIONS

PCT International Search Report and Written Opinion, International Filing Date Dec. 15, 2017; International Application No. PCT/US2017/066560.

\* cited by examiner

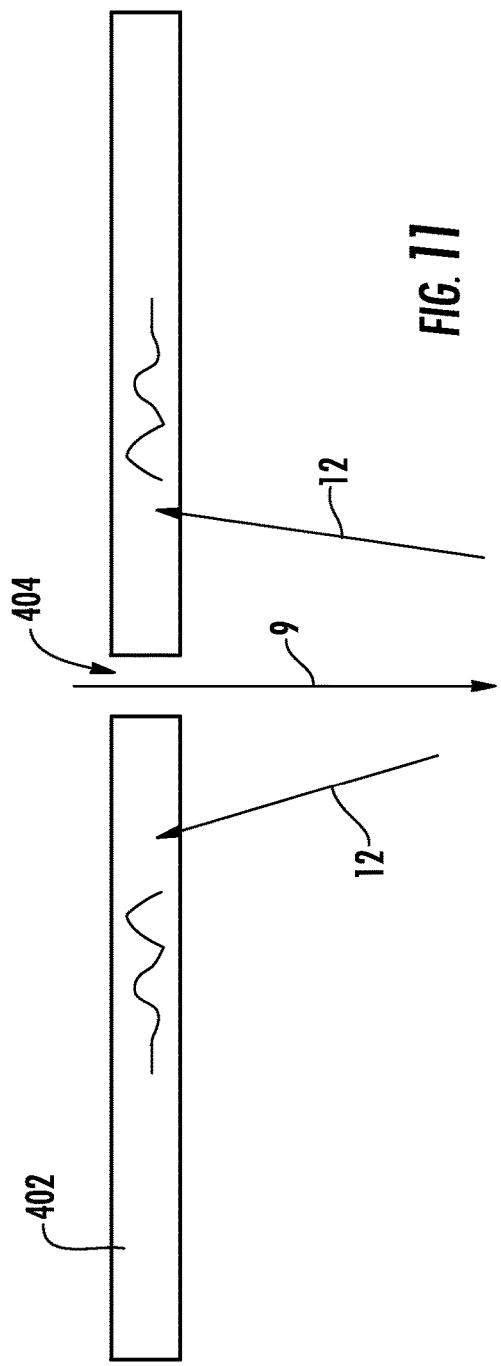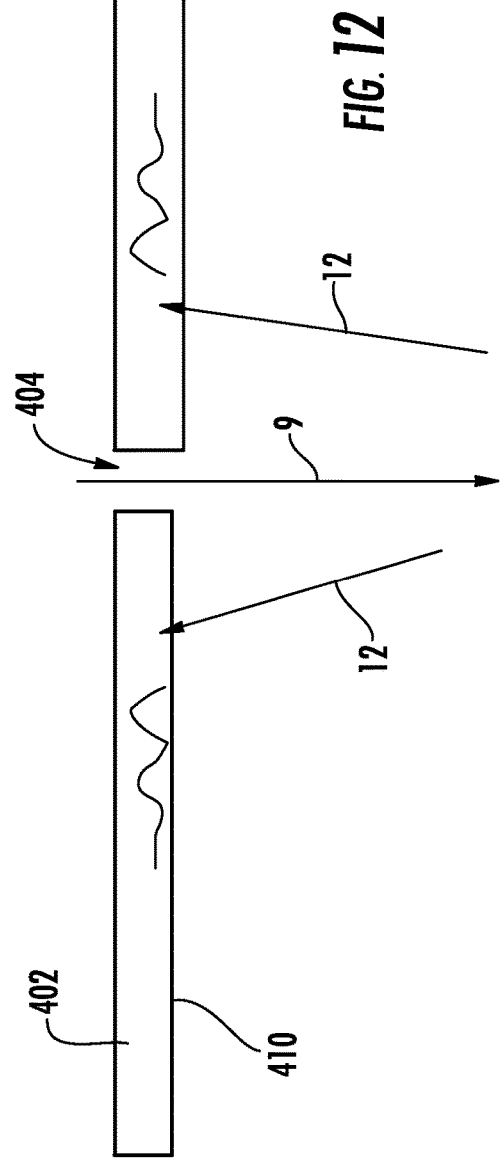

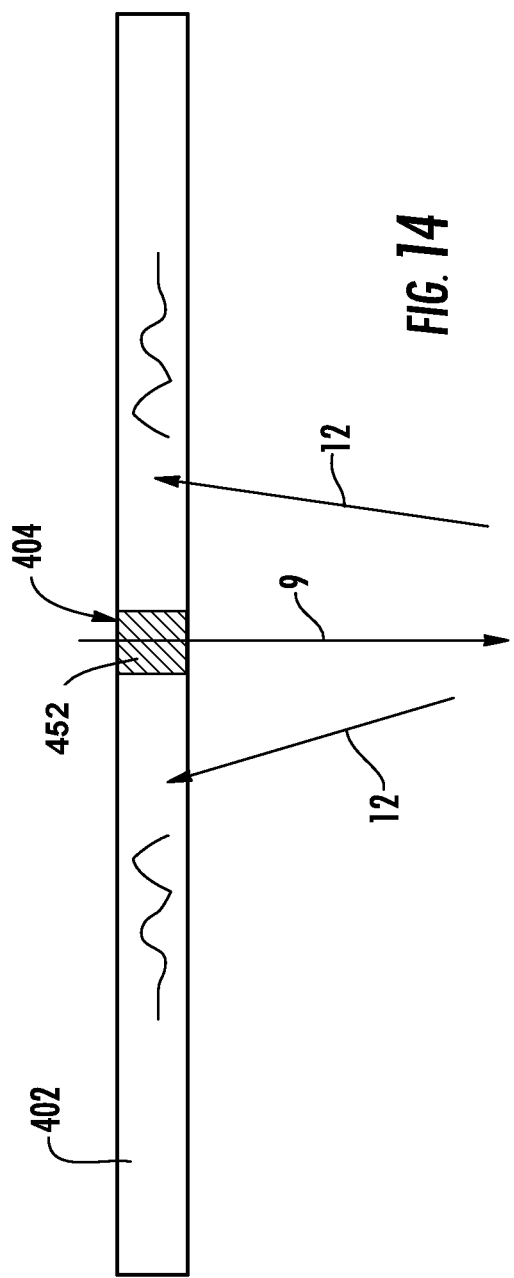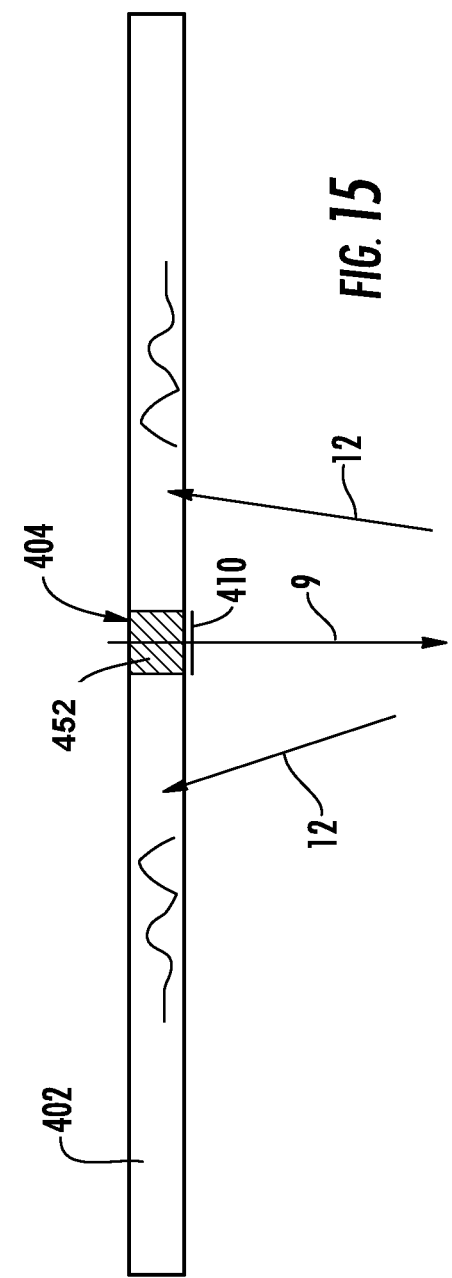

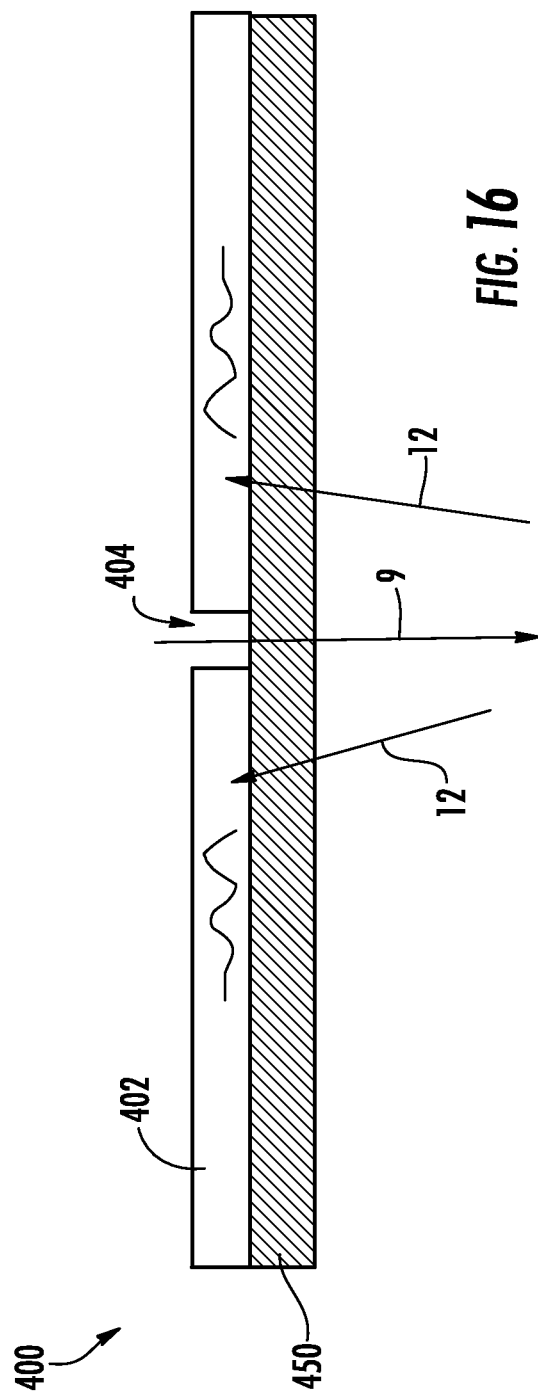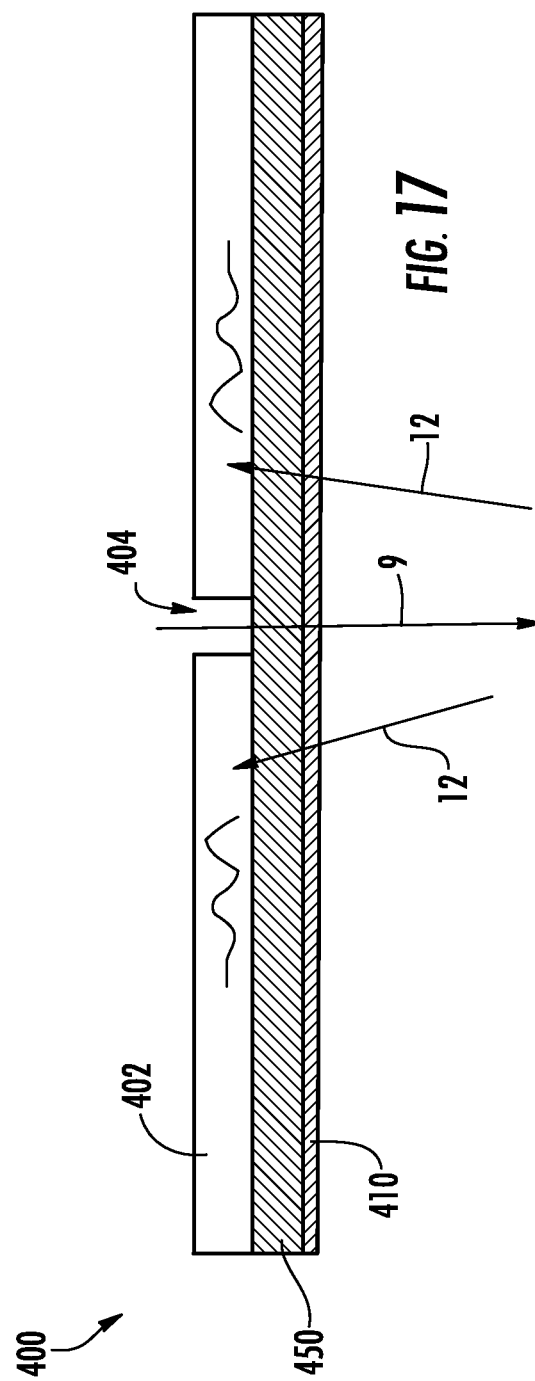

LIGHT CONTROLLING ASSEMBLY FOR AN EGG IDENTIFICATION SYSTEM, AND ASSOCIATED METHOD

CROSS REFERENCE TO RELATED APPLICATION

This application claims the benefit of U.S. Provisional Patent Application No. 62/436,502, filed Dec. 20, 2016, which is expressly incorporated herein by reference in its entirety.

TECHNICAL FIELD

The present disclosure generally relates to egg identification systems. More particularly, the present disclosure relates to an egg identification system having a light controlling assembly capable of improving discrimination among viable and non-viable eggs, and an associated method.

BACKGROUND

Discrimination between poultry eggs on the basis of some observable quality is a well-known and long-used practice in the poultry industry. "Candling" is a common name for one such technique, a term which has its roots in the original practice of inspecting an egg using the light from a candle. As is known to those familiar with eggs, although egg shells appear opaque under most lighting conditions, they are in reality somewhat translucent, and when placed in front of direct light, the contents of the egg can be observed.

Eggs which are to be hatched to live poultry are typically candled during embryonic development to identify clear (infertile), rotted, and dead eggs (collectively referred to herein as "non-live eggs"). Non-live eggs (also referred to as non-viable eggs) are removed from incubation to increase available incubator space and also reduce the risk of biocontamination. In many instances it is desirable to introduce a substance, via in ovo injection, into a live egg (also referred to herein as a viable egg) prior to hatch. Injections of various substances into avian eggs are employed in the commercial poultry industry to decrease post-hatch mortality rates or increase the growth rates of the hatched bird. Examples of substances that have been used for, or proposed for, in ovo injection include vaccines, antibiotics and vitamins.

In commercial poultry production, it is estimated that only about 60% to 90% of commercial broiler eggs hatch. Eggs that do not hatch include eggs that were not fertilized, as well as fertilized eggs that have died. Due to the number of non-live eggs encountered in commercial poultry production, the use of automated methods for in ovo injection, and the cost of treatment substances, an automated method for identifying live eggs and either removing non-live eggs or selectively injecting only live eggs is desirable.

An egg may be a "live" egg, meaning that it has a viable embryo. FIG. 1 illustrates a live poultry egg 1 at about day one of incubation. FIG. 2 illustrates the live egg 1 at about day eleven of incubation. The egg 1 has a somewhat narrow end in the vicinity represented at 10 as well as an oppositely disposed broadened or blunt end portion in the vicinity shown at 20. In FIG. 1, an embryo 2 is represented atop the yolk 3. The egg 1 contains an air cell 4 adjacent to the broadened end 20. As illustrated in FIG. 2, the wings 5, legs 6, and beak 7 of a baby chick have developed.

An egg may be a "clear" or "infertile" egg, meaning that it does not have an embryo. More particularly, a "clear" egg is an infertile egg that has not rotted. An egg may be an "early dead" egg, meaning that it has an embryo which died at about one to five days old. An egg may be a "mid-dead" egg, meaning that it has an embryo which died at about five to fifteen days old. An egg may be a "late-dead" egg, meaning that it has an embryo which died at about fifteen to eighteen days old.

An egg may be a "rotted" egg, meaning that the egg includes a rotted infertile yolk (for example, as a result of a crack in the egg's shell) or, alternatively, a rotted, dead embryo. While an "early dead," "mid-dead" or "late-dead egg" may be a rotted egg, those terms as used herein refer to such eggs which have not rotted. Clear, early-dead, mid-dead, late-dead, and rotted eggs may also be categorized as "non-live" eggs because they do not include a living embryo.

There are other applications where it is important to be able to distinguish between live (viable) and non-live (non-viable) eggs. One of these applications is the cultivation and harvesting of vaccines via live eggs (referred to as "vaccine production eggs"). For example, human flu vaccine production is accomplished by injecting seed virus into a chicken egg at about day eleven of embryonic development (Day-11 egg), allowing the virus to grow for about two days, euthanizing the embryo by cooling the egg, and then harvesting the agnostic fluid from the egg. Typically, eggs are candled before injection of a seed virus to remove non-live eggs. Vaccine production eggs may be candled one or more days prior to injection of a seed virus therein. Identification of live eggs in vaccine production is important because it is desirable to prevent seed vaccine from being wasted in non-live eggs and to reduce costs associated with transporting and disposing of non-live eggs.

Some previous candling apparatuses have employed opacity identification systems in which a plurality of light sources and corresponding light detectors are mounted in an array, and wherein eggs are passed on a flat between the light sources and the light detectors. However, these systems are limited in discriminating among live and non-live eggs, particularly with respect to rotted eggs, in part due to stray light interfering with a desired transmitted signal.

Accordingly, it would be desirable to provide an egg identification system capable of reducing interfering light so that improved discrimination among live and non-live eggs may be achieved. Furthermore, it would be desirable to provide an associated method that would facilitate improved determination and discrimination among live and non-live eggs by improving control of interfering light within an egg identification system.

BRIEF SUMMARY

The above and other needs are met by aspects of the present disclosure which, according to one aspect, provides an egg identification system for determining viability of an avian egg. The system includes an emitter assembly configured to emit electromagnetic radiation toward an egg, the electromagnetic radiation having a predetermined wavelength. A detector assembly is spaced-apart from the emitter assembly and configured to detect electromagnetic radiation transmitted through the egg. A light controlling assembly is positioned proximate to the emitter assembly and is disposed between the emitter assembly and the detector assembly. The light controlling assembly includes an absorbing layer configured to absorb electromagnetic radiation at the predetermined wavelength. The absorbing layer defines an opening through which electromagnetic radiation emitted from the emitter assembly is capable of passing therethrough toward the egg. A processor is configured to process an output signal of the detector assembly to determine viability of the egg.

Another aspect provides a method of determining viability of an egg. The method comprises emitting electromagnetic radiation from an emitter assembly at a predetermined wavelength. The electromagnetic radiation is emitted through an opening defined by an absorbing layer of a light controlling assembly and toward an egg. The method further comprises absorbing, via the absorbing layer, electromagnetic radiation reflected from the egg and other reflective surfaces. The method further comprises detecting electromagnetic radiation transmitted through the egg with a detector assembly spaced-apart from the emitter assembly. The method further comprises generating an output signal from the electromagnetic radiation detected by the detector assembly. The method further comprises processing the output signal to determine viability of the egg.

Thus, various aspects of the present disclosure provide advantages, as otherwise detailed herein.

BRIEF DESCRIPTION OF THE DRAWINGS

Figure 1:
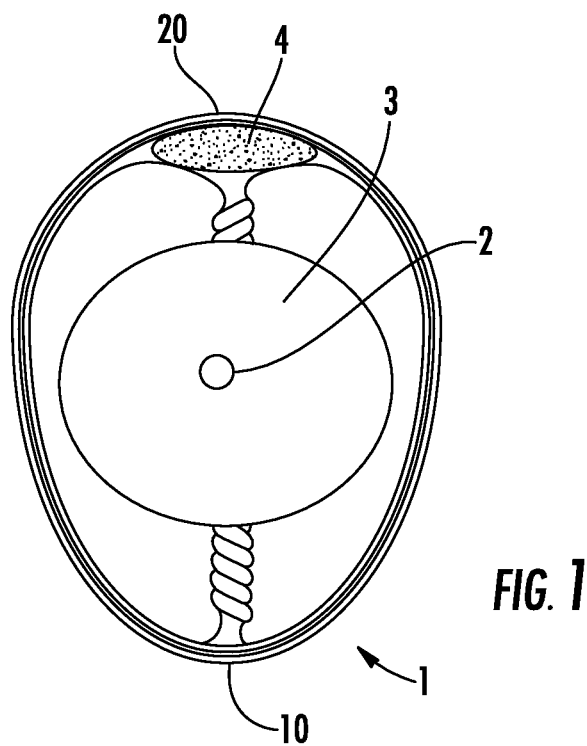
Figure 2:
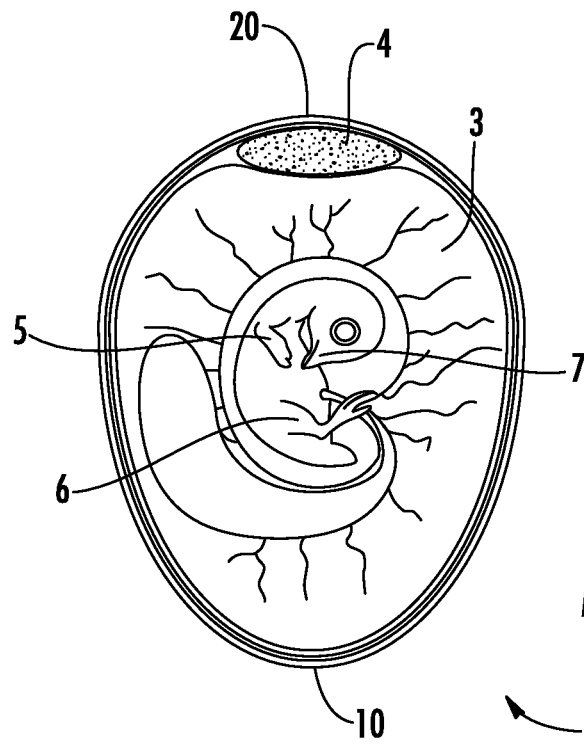
Figure 3:
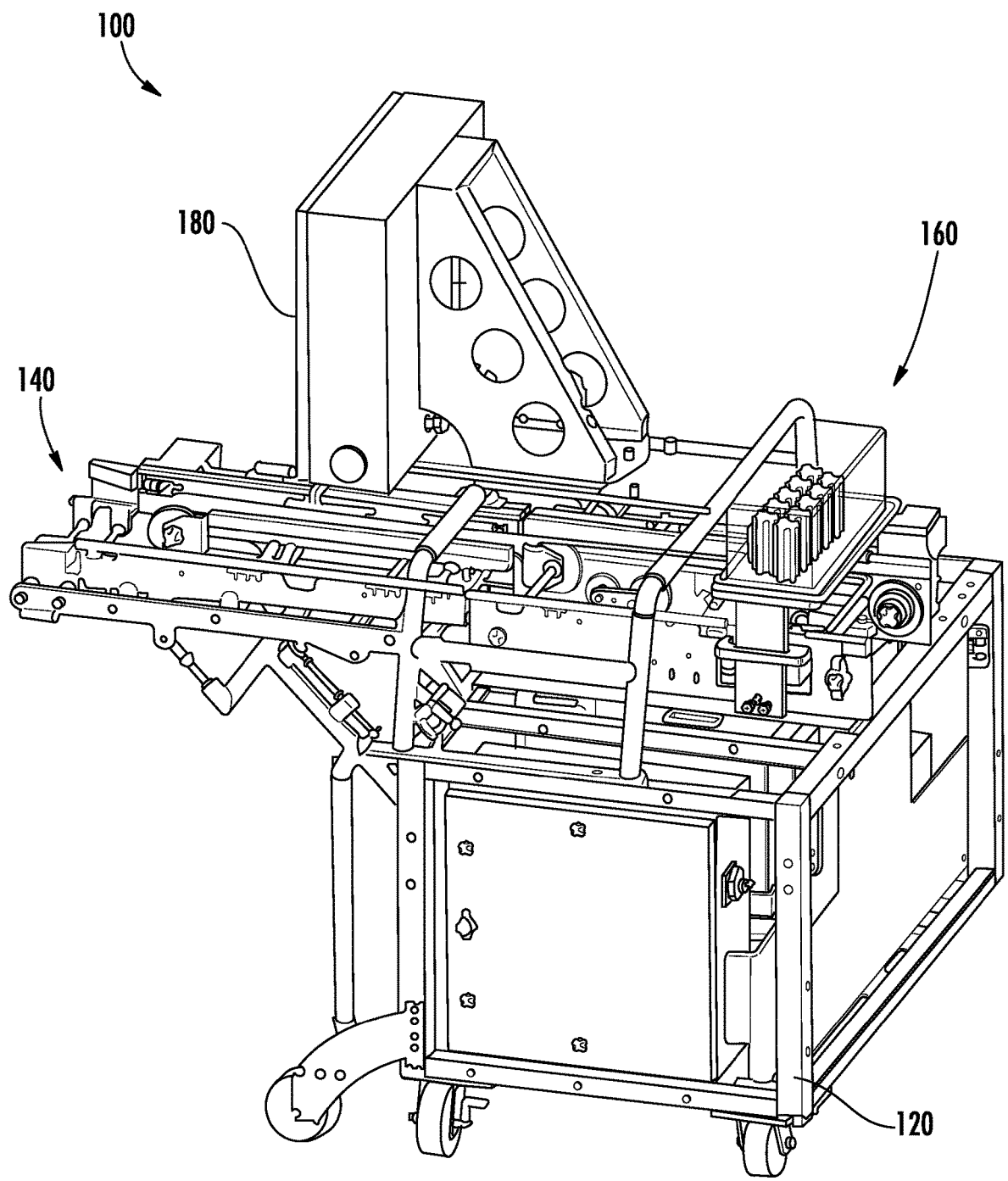
Figure 4:
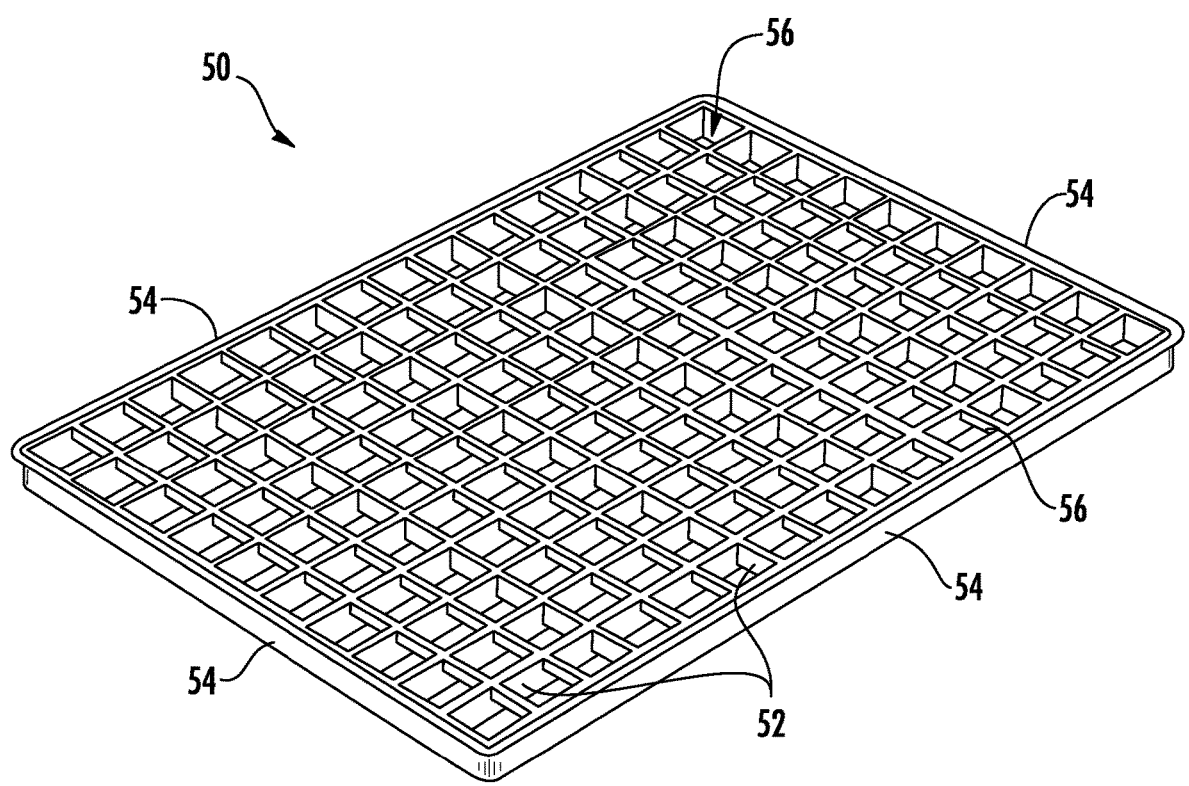
Figure 5:
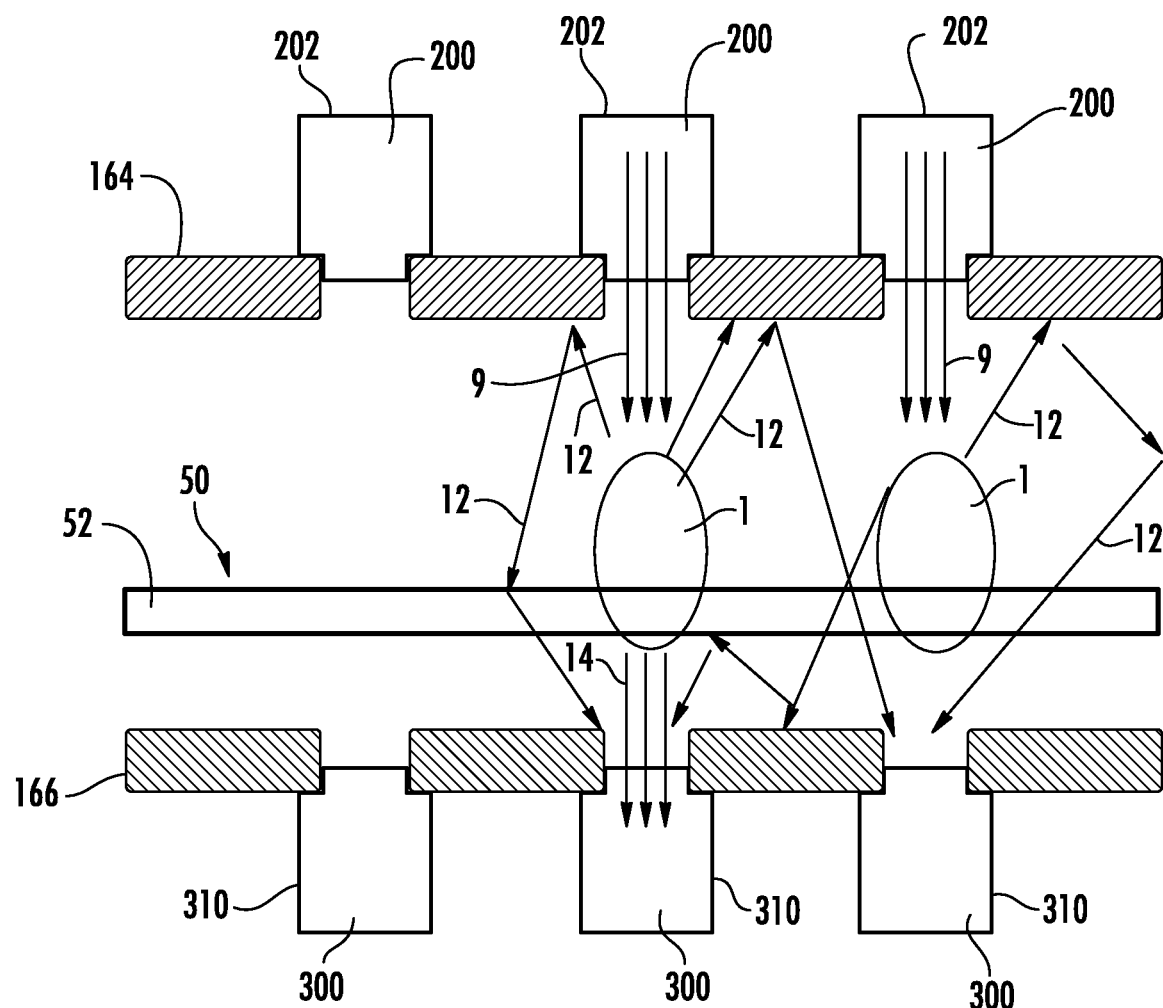
Figure 6:
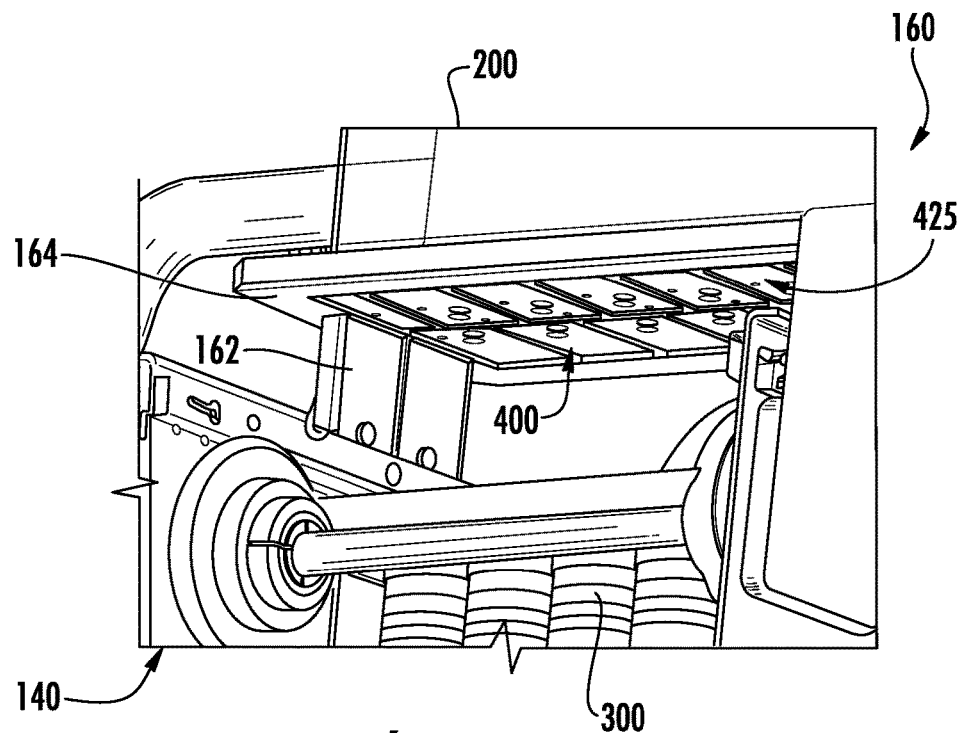
Figure 7:
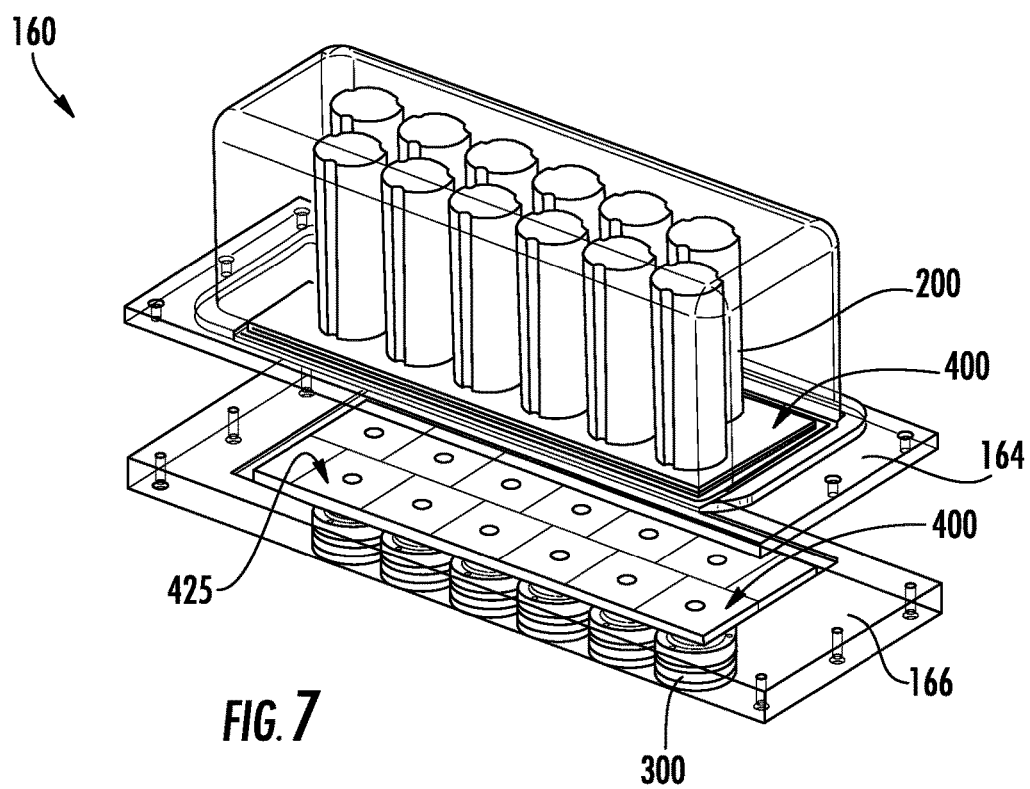
Figure 8:
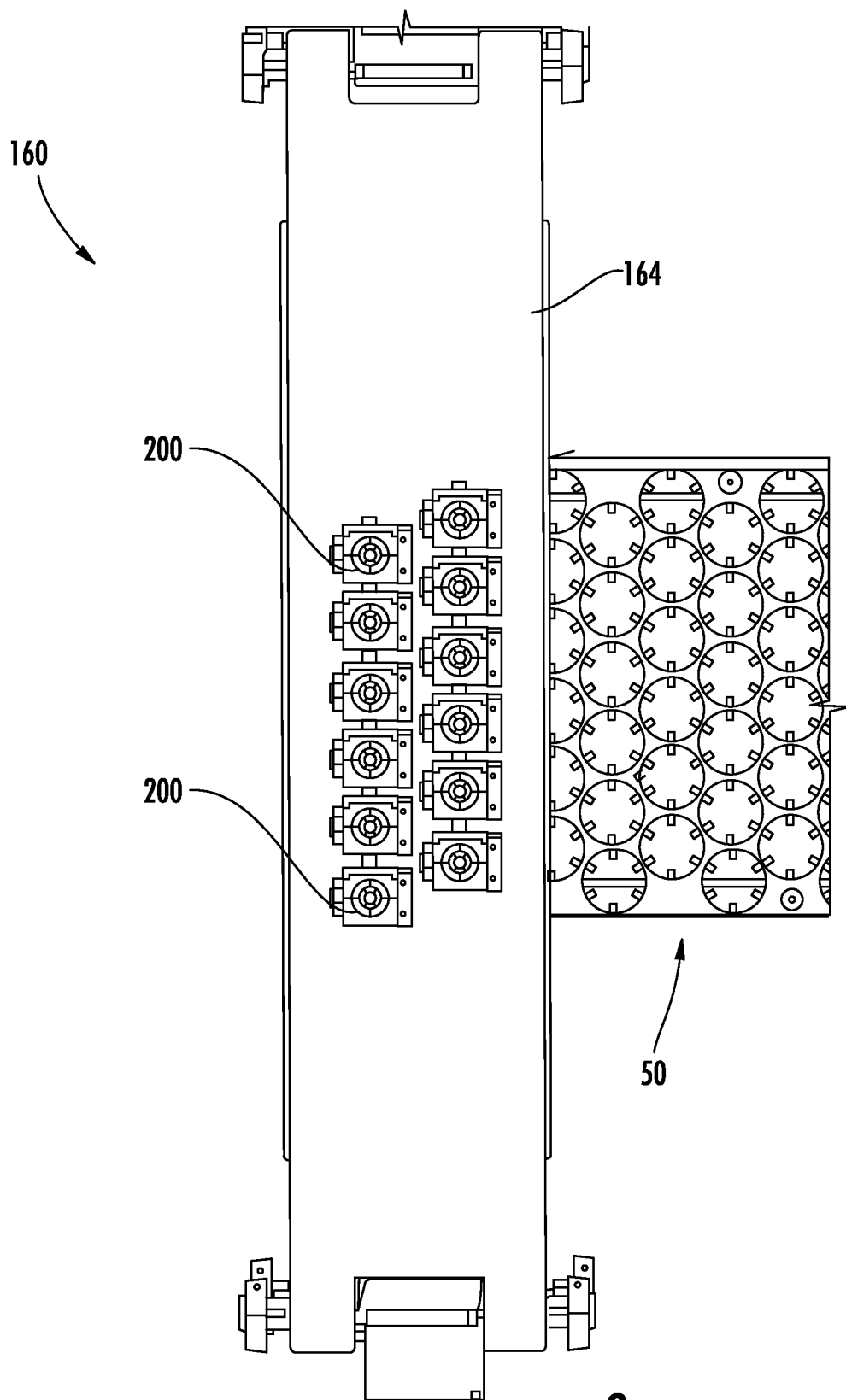
Figure 9:
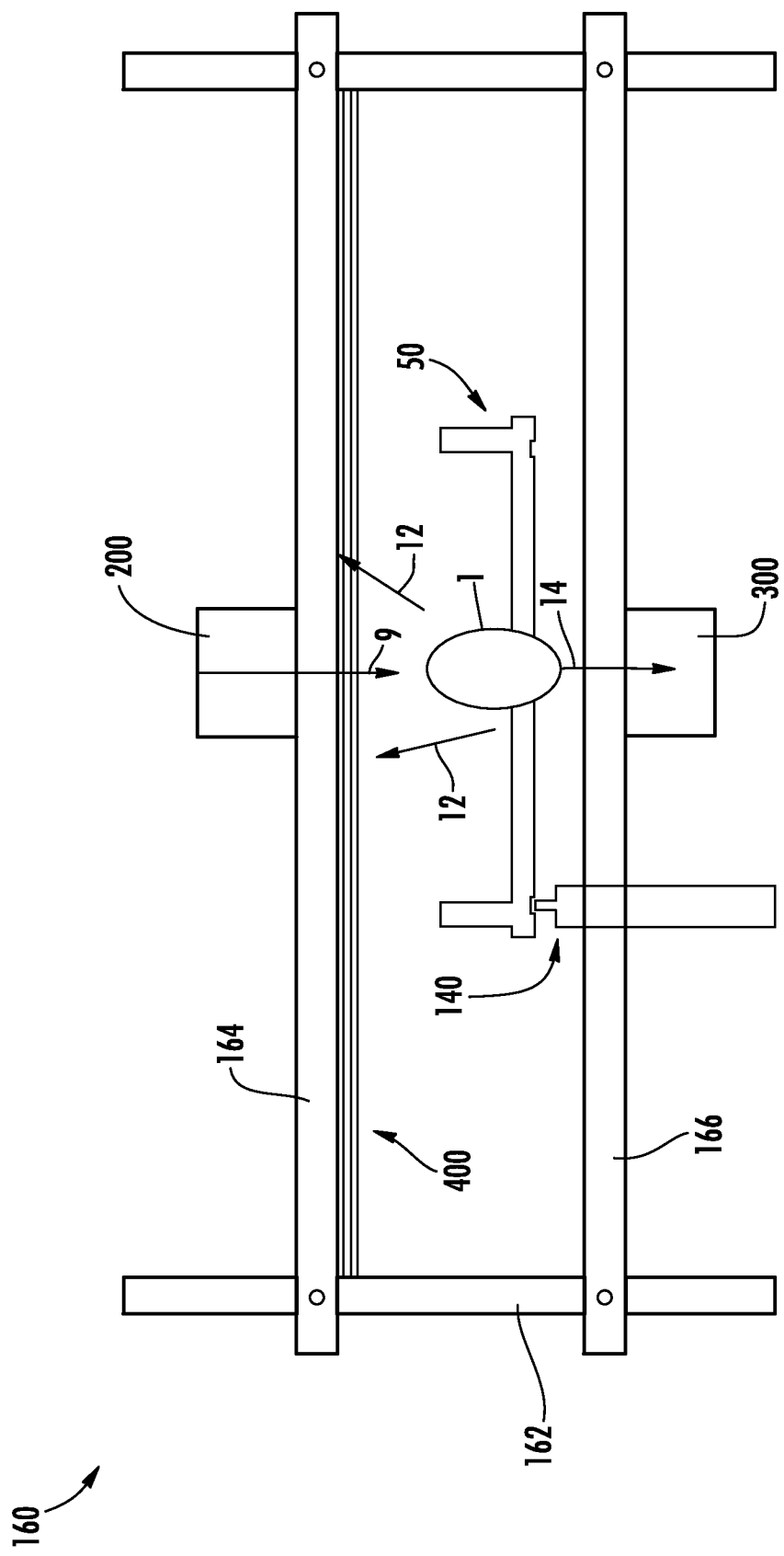
Figure 10:
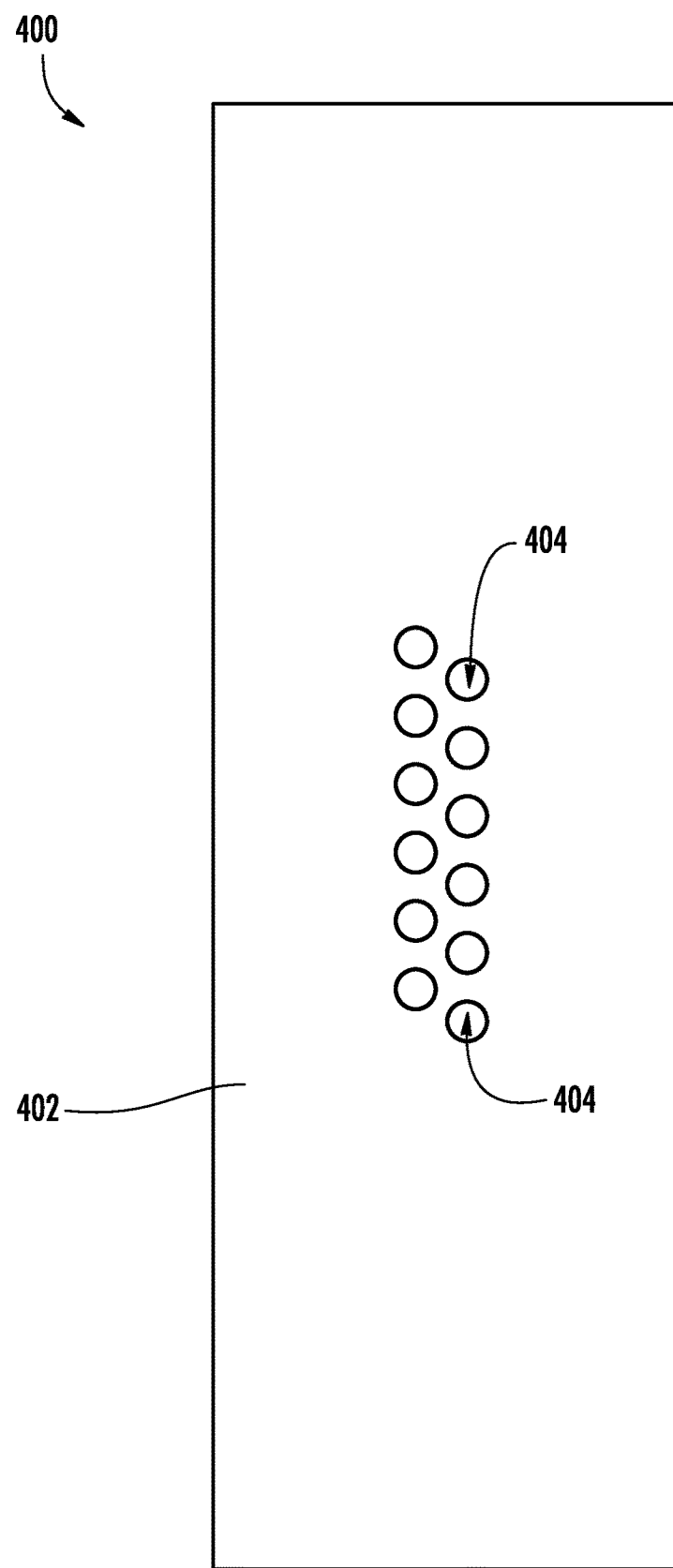
Figure 13:
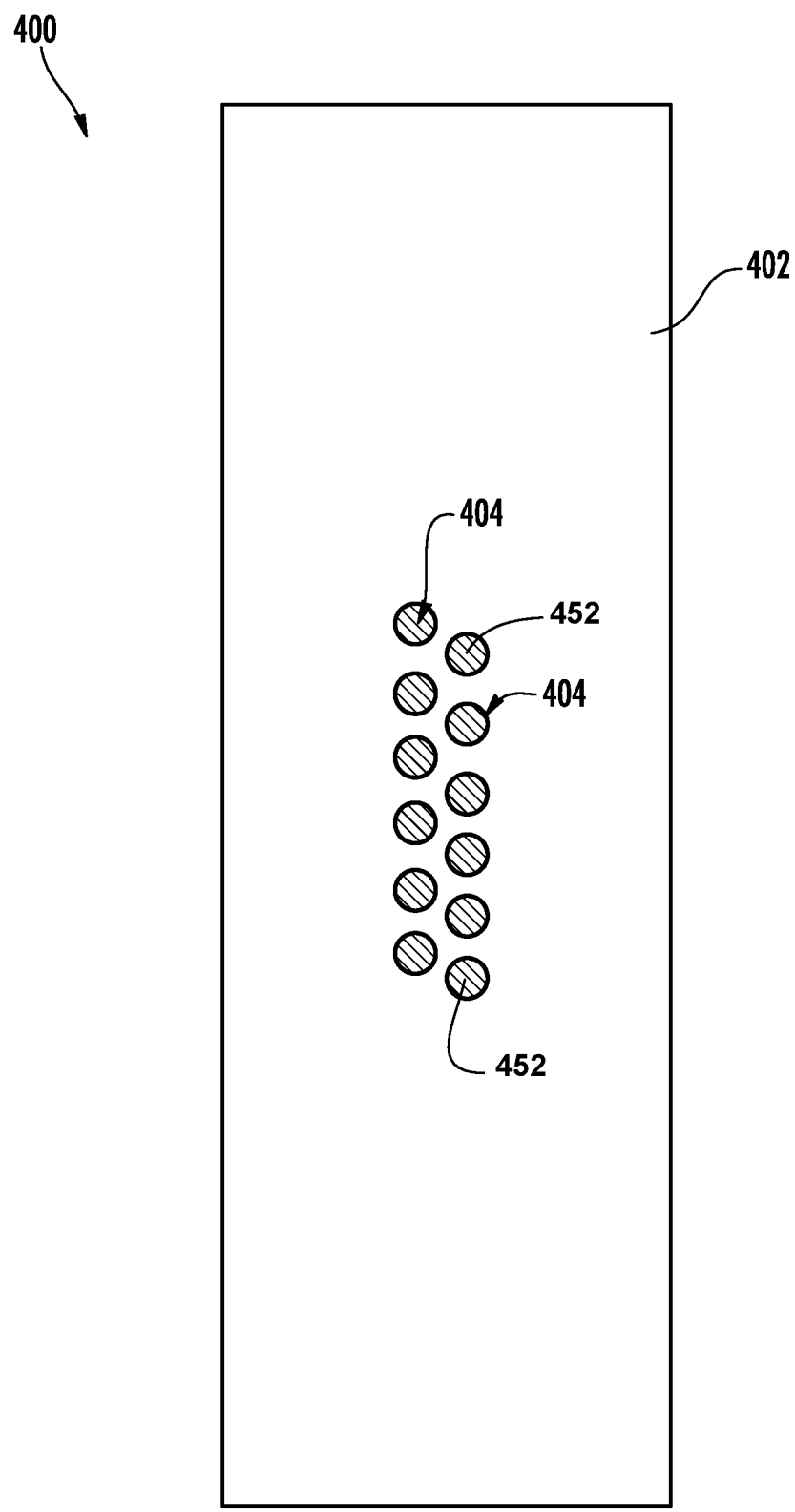
Figure 18:
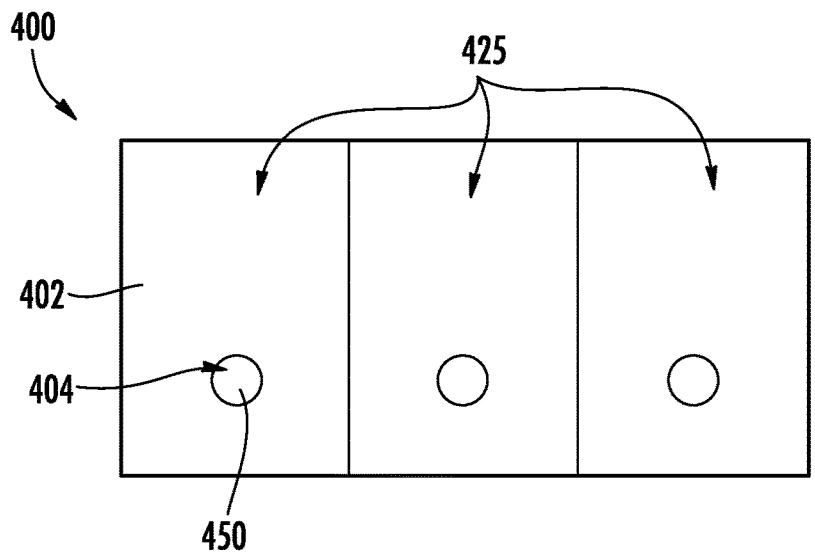
Figure 19:
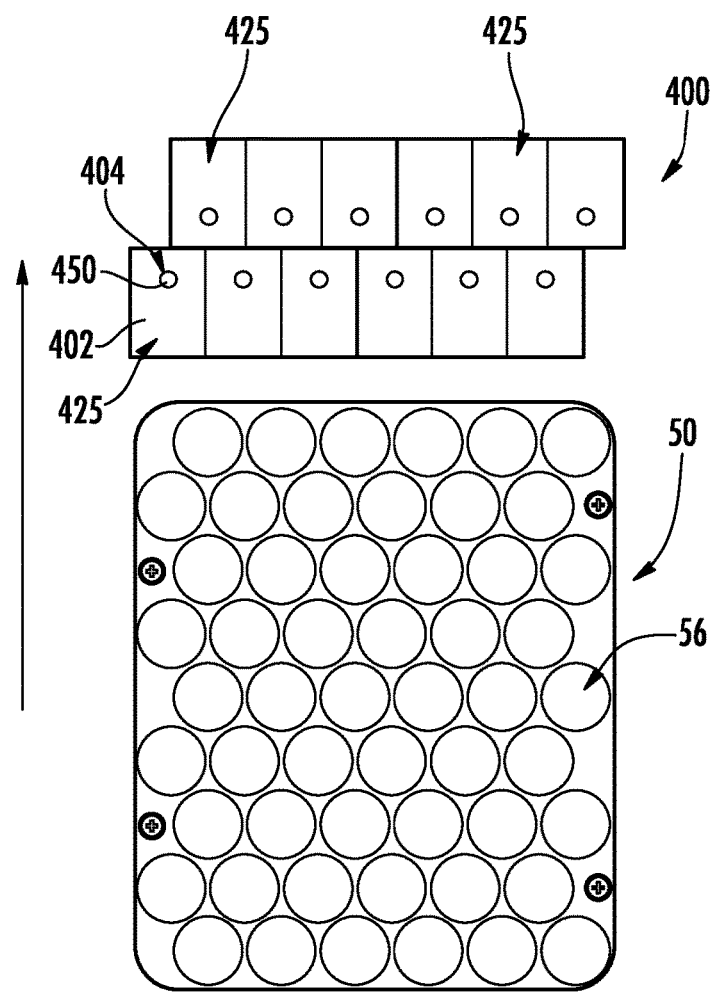
Figure 20:
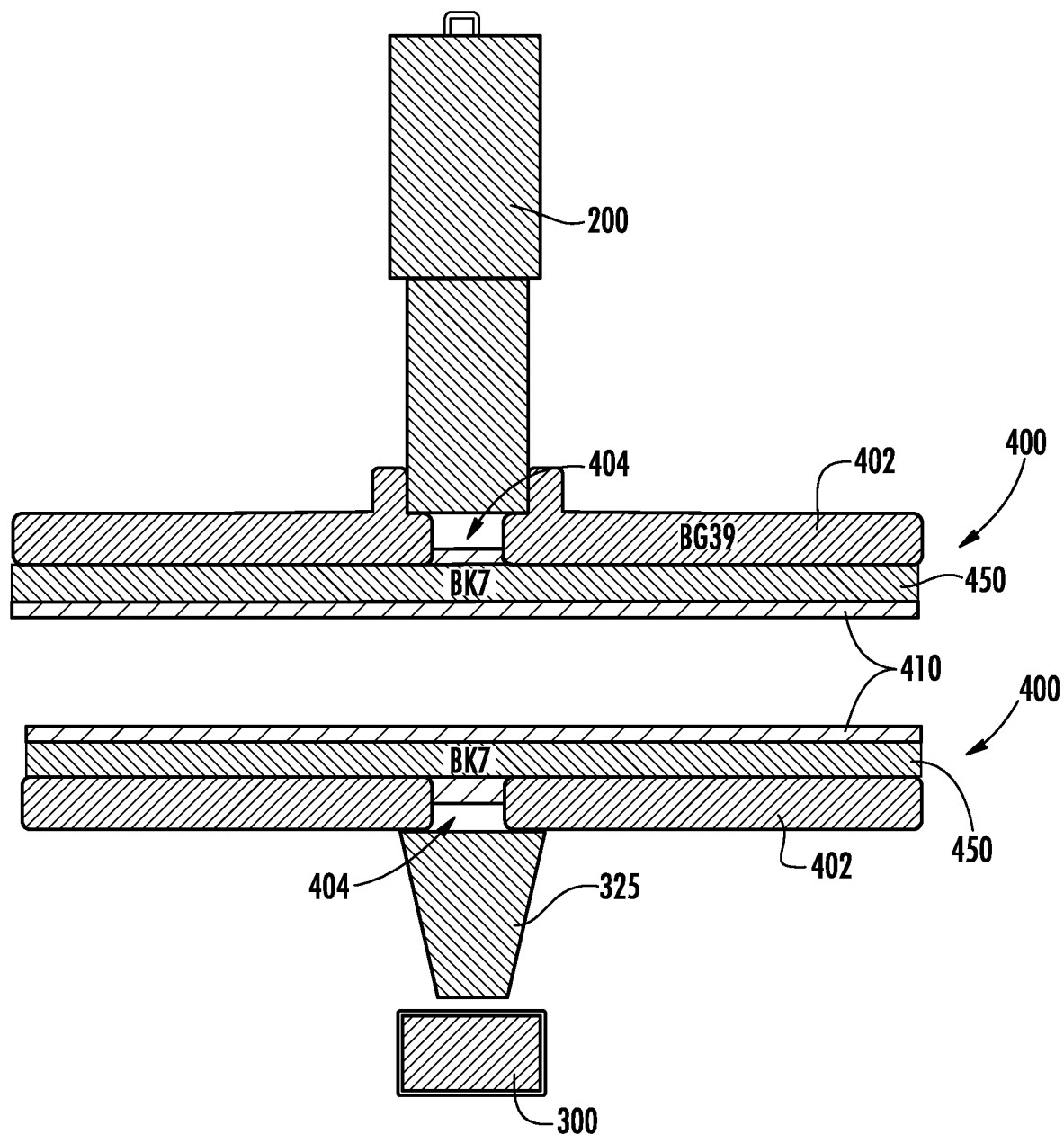
Figure 21:
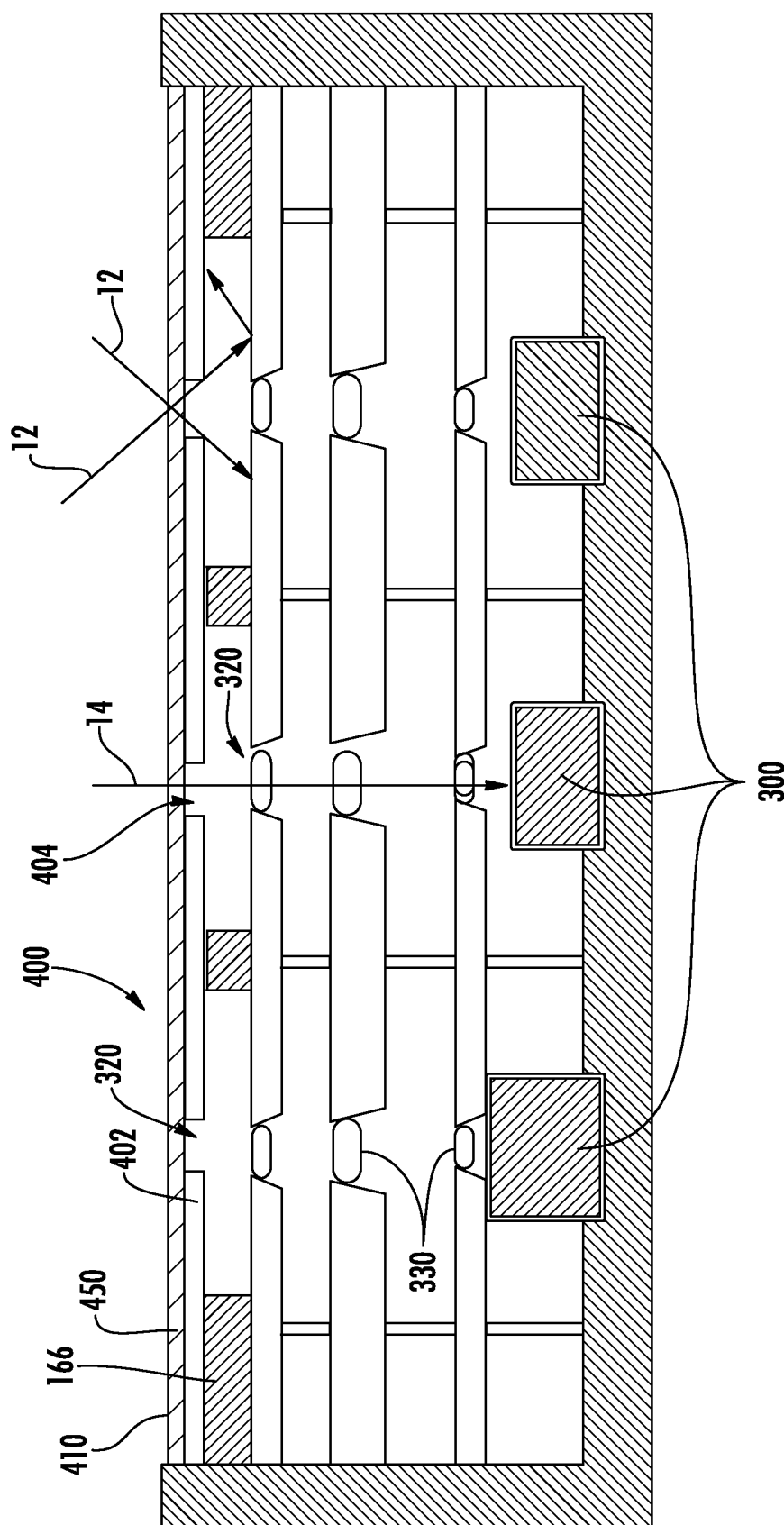
Figure 22:
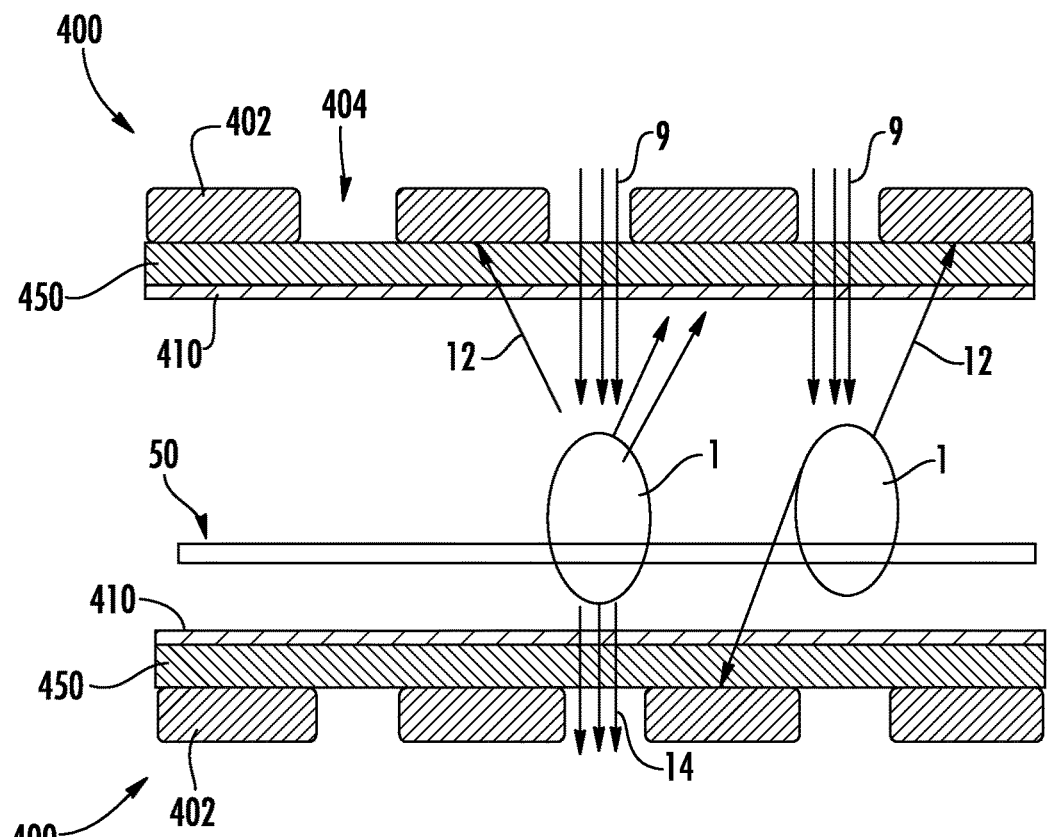
Figure 23:
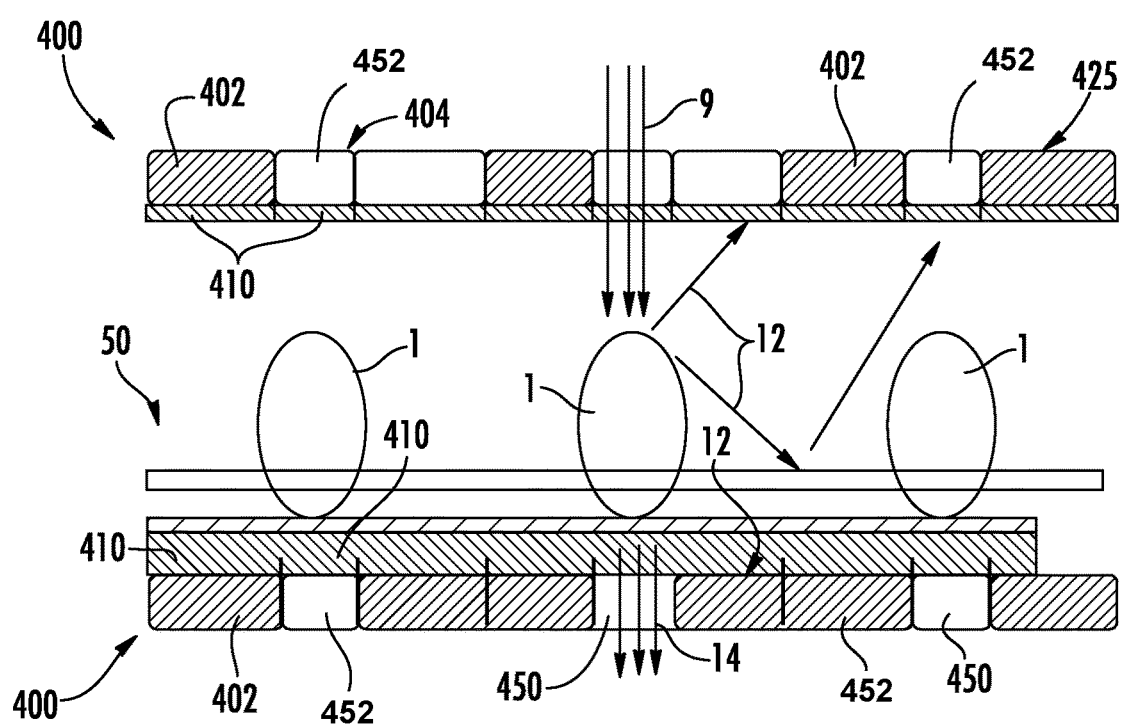
Figure 24:
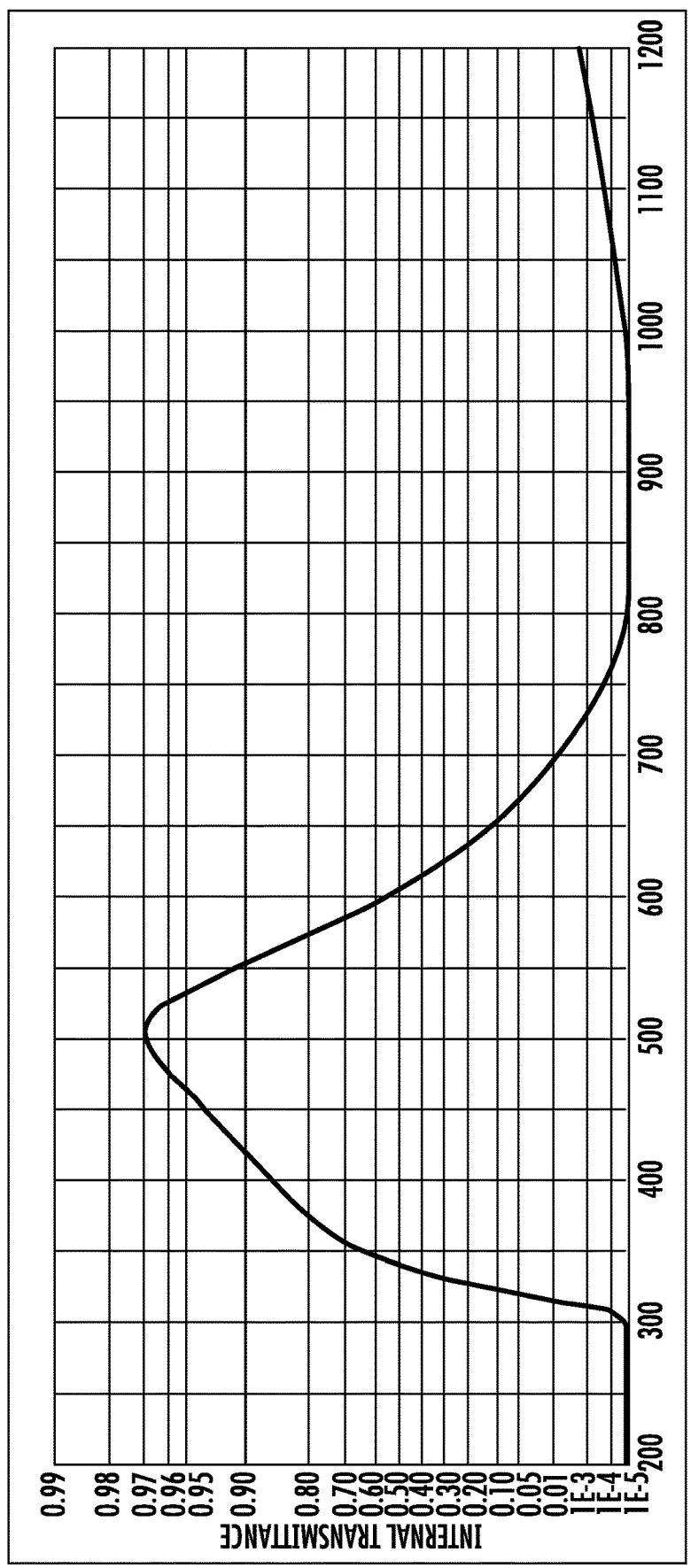
Figure 25:
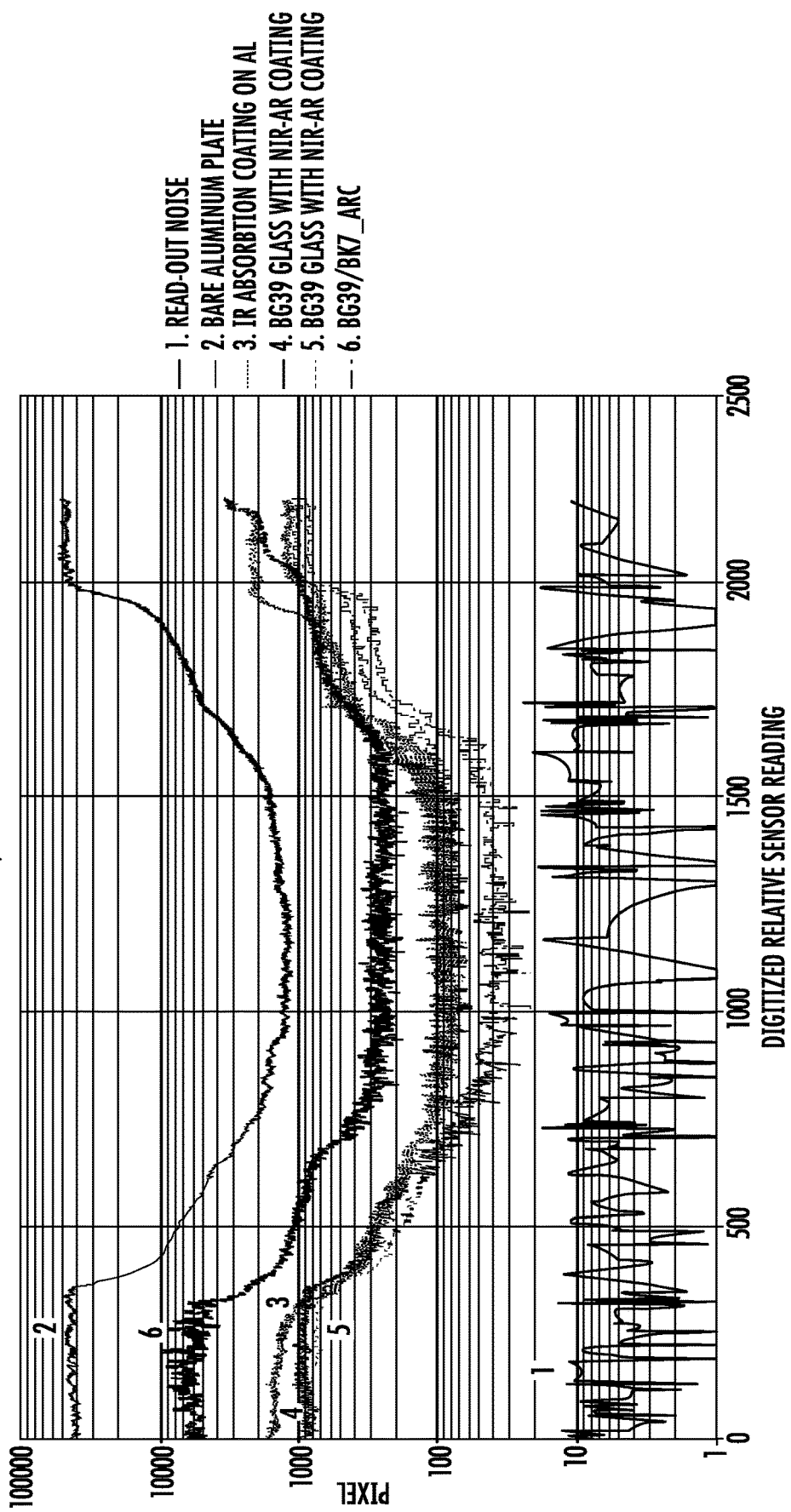
Figure 26:
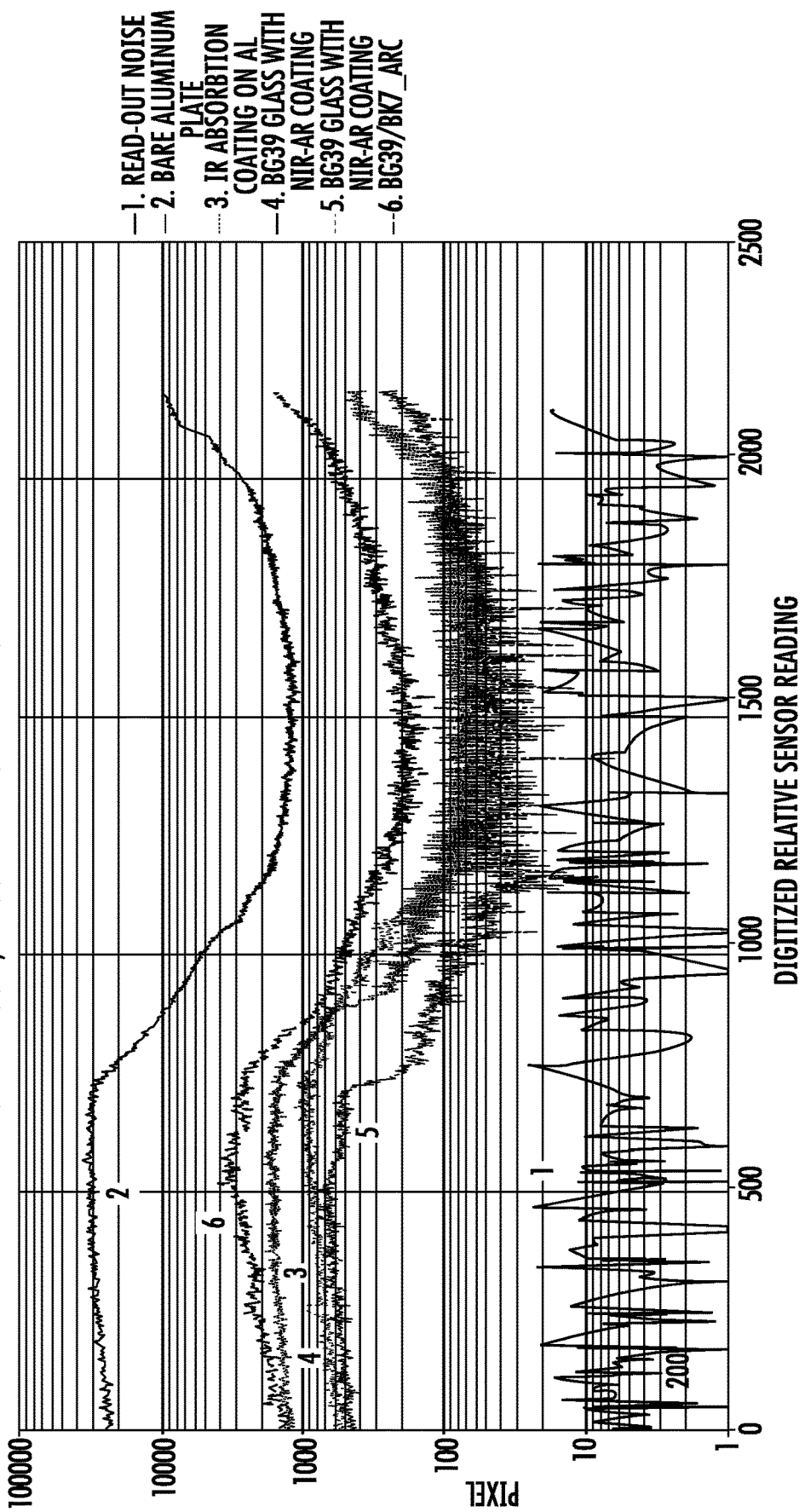

Having thus described various embodiments of the present disclosure in general terms, reference will now be made to the accompanying drawings, which are not necessarily drawn to scale, and wherein:

FIG. 1 illustrates a live chicken egg at about day one of incubation;

FIG. 2 illustrates a live chicken egg at about day eleven of incubation;

FIG. 3 is a schematic perspective view of an egg identification system, according to one aspect of the present disclosure;

FIG. 4 is a perspective schematic view of an egg flat capable of containing eggs in a fixed position;

FIG. 5 illustrates eggs in an egg flat being conveyed past a series of emitter-detector pairs of an egg detection system, and further illustrating paths of interference of off-axis emissions that undesirably contribute to a detected signal;

FIG. 6 is a partial schematic perspective view of an egg identification system having a light controlling assembly, according to one aspect of the present disclosure;

FIG. 7 is a partial schematic perspective view of an egg identification device, according to one aspect of the present disclosure;

FIG. 8 is a partial plan view of an egg identification system having a light controlling assembly, according to one aspect of the present disclosure;

FIG. 9 illustrates an egg being investigated for viability by an emitter-detector pair capable of use in an egg identification system having a light controlling assembly, according to one aspect of the present disclosure;

FIG. 10 is a schematic plan view of a light controlling assembly for an egg identification system, according to one aspect of the present disclosure;

FIG. 11 is a partial cross-sectional view of a light controlling assembly for an egg identification system, according to one aspect of the present disclosure;

FIG. 12 is a partial cross-sectional view of a light controlling assembly for an egg identification system, according to another aspect of the present disclosure;

FIG. 13 is a schematic plan view of a light controlling assembly for an egg identification system, according to another aspect of the present disclosure;

FIG. 14 is a partial cross-sectional view of a light controlling assembly for an egg identification system, according to one aspect of the present disclosure;

FIG. 15 is a partial cross-sectional view of a light controlling assembly for an egg identification system, according to another aspect of the present disclosure;

FIG. 16 is a partial cross-sectional view of a light controlling assembly for an egg identification system, according to one aspect of the present disclosure;

FIG. 17 is a partial cross-sectional view of a light controlling assembly for an egg identification system, according to another aspect of the present disclosure;

FIG. 18 is a schematic view of a segmented light controlling assembly, according to another aspect of the present disclosure;

FIG. 19 illustrates the alignment of a segmented light controlling assembly with an egg flat used to carry eggs, according to another aspect of the present disclosure;

FIG. 20 is a schematic cross-sectional view of an egg identification device having a light controlling assembly associated with an emitter assembly and a detector assembly, according to another aspect of the present disclosure;

FIG. 21 is a schematic cross-sectional view of an egg detector system having a light controlling assembly, according to one aspect of the present disclosure;

FIGS. 22 and 23 illustrate eggs being investigated for viability by emitter-detector pairs capable of use in an egg identification system having multiple light controlling assemblies, according to one aspect of the present disclosure;

FIG. 24 is a graph illustrating the internal transmittance of an absorbing material (BG-39) capable of use in a light controlling assembly as a function of the wavelength of light; and FIGS. 25 and 26 are graphs providing a comparison of absorption characteristics of various light controlling assemblies and against a system without a light controlling assembly.

DETAILED DESCRIPTION OF THE DISCLOSURE

Various aspects of the present disclosure now will be described more fully hereinafter with reference to the accompanying drawings, in which some, but not all aspects of the disclosure are shown. Indeed, this disclosure may be embodied in many different forms and should not be construed as limited to the aspects set forth herein; rather, these aspects are provided so that this disclosure will satisfy applicable legal requirements. Like numbers refer to like elements throughout.

The present disclosure is directed to systems and methods for improving accuracy in determining the viability of eggs as the eggs pass through an identification means. Eggs may be passed through the system in a contact or non-contact manner. Non-contact provides many advantages, including maintaining stationary position of the detection system components to improve throughput and limiting contact with non-live eggs such as rotted eggs that may explode. As used herein, the term "non-contact" refers to maintaining a spaced-apart relationship between the egg and components of the egg identification system disclosed herein during operation of the emitter-detector pairs when determining viability. In this regard, the emitter assembly and the detector assembly of the present disclosure may be positioned apart from the egg such that no component thereof contacts the egg, thereby eliminating any mechanical light seal capable of limiting interfering signals from being detected. Instead, the present disclosure deals with rejecting these interfering signals by other means. However, in some instances, a mechanical light seal may be used in conjunction with the emitter assembly and/or the detector assembly.

In some instances, the present disclosure may be directed to systems and methods using transmission modes for determining viability of an egg. By operating in a transmission mode, the emitter and detector of the egg identification system may be axially aligned along a common longitudinal axis such that the system may be configured in a workable manner. That is, the emitter assembly and the detector assembly may be positioned on opposite sides of the eggs such that the eggs can easily pass therebetween for evaluation and identification.

Because aspects of the present disclosure may operate in a non-contact and transmission manner, the desired transmitted light levels may be low while the potential for undesirable interference signals may be high. In this regard, aspects of the present disclosure are provided such that the undesired interference signal may be limited and the desired transmission signal may be maximized for processing so as to provide reliable identification of viable and non-viable eggs within an acceptable level of accuracy.

The methods and systems according to aspects of the present disclosure may be utilized for improving identification of live and non-live eggs at any time during embryonic development (also referred to as the incubation period). Aspects of the present disclosure are not limited to identification only at a particular day (e.g., day eleven) or time period during the embryonic development period. In addition, methods and apparatus according to aspects of the present disclosure may be used with any types of avian eggs including, but not limited to, chicken, turkey, duck, geese, quail, pheasant eggs, exotic bird eggs, etc.

FIG. 3 illustrates an egg identification system 100 capable of implementing various aspects of the present disclosure. The egg identification system 100 may include a frame 120 and a conveyor system 140 configured to convey a plurality of eggs contained in an egg flat 50 (FIG. 4) to an egg identification device 160. In some instances, the egg identification system 100 may include a display 180 capable of displaying information related to the egg identification system 100 and/or the eggs passing through the egg identification device 160 for identification thereof. The egg identification system 100 may include a controller for controlling various aspects of thereof, including the ability to enable and disable certain components of the egg identification device 160. The egg identification system 100 may be portable and, in some instances, may be configured in a modular manner such that it may be connected to other associated devices, such as, for example, an egg injection apparatus, an egg sorting apparatus, an egg transfer apparatus, an egg remover apparatus, or a gender identification apparatus. In some instances, the egg identification device 160 may be directly applied to an egg injection apparatus, an egg sorting apparatus, an egg transfer apparatus, an egg remover apparatus, or a gender identification apparatus.

Referring to FIG. 4, the egg flat 50 may be formed of a plurality of intersecting slats 52 confined by a plurality of ends 54. The slats 52 may define a plurality of open-ended pockets 56, with each pocket 56 capable of receiving an end of a respective egg 1. In some instances, the narrow end 10 (FIGS. 1 and 2) of the egg 1 may be received within the pocket 56 such that the blunt end 20 projects above the egg flat 50.

Referring now to FIG. 5, two emitter-detector pairs for use in classifying eggs, according to some aspects of the present disclosure, are illustrated. The illustrated emitter-detector pairs may each include an emitter assembly 200 and a detector assembly 300. In operation, a plurality of the emitter-detector pairs may be arranged in an array and utilized to classify a respective array of eggs supported by an egg flat 50 (FIG. 4). The illustrated emitter assembly 200 may include an emitter housing 202. Aspects of the present disclosure are not limited to the illustrated configuration of the emitter housing 202. The emitter housing 202 may have various shapes, sizes and configurations without limitation. An array of the emitter assemblies 200 may be supported via a frame or other supporting member of the egg identification device 160. When the egg identification device 160 is configured to operate in a non-contact manner, the emitter assemblies 200 may not need to move between a raised position and a lowered position, although in some instances each may be configured for such movement to contact or become proximately positioned to the egg.

Disposed within the emitter housing 202 is a light emission source. The light emission source may be configured to emit electromagnetic radiation of various wavelengths of the electromagnetic spectrum, including, for example, visible light, infrared light and near-infrared light. In some instances, the light emission source may be particularly configured to emit infrared light in the wavelength range of about 800 nanometers to 1000 nanometers (nm), and more particularly at 800-810 nm or 900-1000 nm. More specifically, in some instances, the electromagnetic radiation may be emitted at about 808 nanometers, about 904 nanometers, or about 980 nanometers. According to some aspects, the light emission source may be formed of a light emitting diode (LED) configured to emit light from the infrared portion of the electromagnetic spectrum. However, aspects of the present disclosure are not limited to the use of LEDs or infrared radiation. Various types of light emission sources may be utilized without limitation, such as, for example, a laser source or a solid-state excitation source, such as an LD. The optical power of the electromagnetic radiation should be sufficient to pass through an egg.

FIG. 5 illustrates some various potential emission paths that the electromagnetic radiation emitted by the light emission source may travel when exiting the emitter assembly 200. Emitted light 9 is transmitted through the egg and detected by the detector assembly 300. As mentioned previously, detecting the transmitted light levels transmitted through the egg 1 without the use of a mechanical light seal provides a challenge. In light of the absence of mechanical light seals, aspects of the present disclosure may be configured to minimize the detection of interfering reflective signals 12 by minimizing stray light from impinging on a detector field of view (FOV) of the detector assembly 300. In this regard, aspects of the present disclosure may be configured to maximize desired signal collection while simultaneously maximizing elimination of undesired signals to attain a desired signal-to-interference (S/I) ratio, with or without the use of mechanical light seals.

The emitter assembly 200 may be configured to maximize emission of the electromagnetic radiation along a longitudinal axis of the egg 1 such that the emissions are directed toward the egg 1. In some instances, the emitter assembly 200 may be configured to collimate or focus the light into a directed beam so as to project the emission of the light emission source onto a prescribed region of the egg 1, while limiting the emission of stray light, wherein stray light is any optical energy leaving the emitter assembly 200 that does not illuminate the prescribed region of the egg (or light that reflects from the prescribed region of the egg). In some instances, however, optomechanical features may be provided for defocusing the beam as well.

The present disclosure may also include a detector assembly 300 for receiving electromagnetic radiation/light 14 transmitted through the egg during the candling operation. The detector assembly 300 may be spaced-apart from the emitter assembly 200 so as to form an emitter-detector pair. Thus, a plurality of emitter assemblies 200 and a respective plurality of detector assemblies 300 may form an array of emitter-detector pairs capable of evaluating a plurality of eggs transported in an egg flat. The emitter assembly 200 and detector assembly 300 may be in axial alignment (on opposite ends of the egg) in some instances and in other instances may be arranged in an off-axis orientation. The detector assembly may be configured to detect electromagnetic radiation/light 14 at a particular wavelength or otherwise within a predetermined range of wavelengths.

As discussed previously, in some instances, the detector assembly 300 may be spaced-apart from the egg during the candling operation such that no part of the detector is in contact with the egg, thereby defining a non-contact position. Such a contactless configuration may allow for increased throughput and may limit contamination of subsequent eggs, as described previously.

The detector assembly 300 may include photodetection means for detecting and carrying out photoelectric conversion of the light transmitted through the egg. For example, a sensor having a photodetector (e.g., a PIN diode) and associated components capable of assisting with generation of an output signal corresponding to the light leaving an egg may be provided. The sensor may be any type of sensor capable of detecting the wavelength(s) of light emitted by the light emission source at modulation frequencies, including DC. According to some aspects, detector assembly 300 may not use any optical elements to collect the optical energy from the egg 1, so as to be a so-called "passive" sensor. In general, the purpose of the sensor may be to detect illumination emitted from a restricted region (field of view) of the egg 1. The detector assembly may include a detector housing 310 in which the sensor may be disposed to receive light leaving an egg 1.

The detector assembly 300 may include one or more lenses, vanes and/or apertures for rejecting stray or off-axis light capable of entering the detector assembly 300 along undesired paths, while allowing desired transmitted light to be collected from the detector field of view on the narrow end 10 of the egg 1. According to some aspects, as shown in FIG. 21, the detector assembly 300 may utilize optical elements or a detector lens system to collect light from a prescribed region on the egg 1 (the detector field of view) and deliver it to the sensor. In this regard, mechanical features such as apertures and lens cells may be included to improve performance of the detector assembly 300. The plates holding the lens may be made of, or otherwise layered with, a light absorbing material such as glass. The surface may have an anti-reflective coating. The residual surface reflection may be made as specular (mirror like) as possible in order that reflected light continues away from the entrance aperture. Unique carrier frequencies of the emitters permit adjacent detectors to reject light from all but the respective paired emitter. The end plates may be made of the light absorbing material, and may have an anti-reflective coating since the reflection will reverse the direction of the light.

In operation, once an egg 1 is disposed between the emitter-detector pair, the light emission source may emit light (indicated as 10 in FIG. 5) toward the egg 1. The sensor may receive light that leaves the egg 1 (indicated as 15 in FIG. 5) and may generate an output signal corresponding to the optical power or other output of the light leaving the egg 1.

A processor may be in communication with the detector assembly 300 and configured to process output signals from the sensor to determine the viability of the egg 1. Appropriate circuitry may be in communication with the sensor (e.g., a photodetector) configured to generate an output signal transmitted to the processor 600. Viability may be determined by processing the output signal to determine variations in optical power corresponding to embryo viability. For example, the optical power of light passing through an egg may be determined at a desired wavelength or signature wavelength, and a spectrum that represents optical power at a selected wavelength may be generated. The generated spectrum may then be compared with one or more spectra associated with a respective known egg condition to identify a present condition of the egg. For example, the generated spectrum may be compared with a respective spectrum associated with one or more of the following: live eggs, early dead eggs, middle dead eggs, late dead eggs, clear eggs, rotted eggs, and/or missing eggs.

According to some aspects of the present disclosure, the egg identification device 160 may be capable of identifying eggs according to viability while in motion as passing through the egg identification system 100. In this regard, the eggs 1 in the egg flat 50 may be capable of being moved through the egg identification system 100 during viability evaluation thereof, thereby allowing for an optimal throughput as desired. To that end, the egg flat 50 may need to be stopped or paused during identification processing to allow for sufficient data collection.

According to aspects of the present disclosure, the egg identification device 160 may include a light controlling assembly 400 provided for reducing the stray light detectable by the detector assembly 300. As shown in FIGS. 6-23, the light controlling assembly 400 may be provided as a plate 402 or generally planar structure, although the present disclosure is not limited to such configurations.

In some instances, as shown in FIGS. 10 and 11, the light controlling assembly 400 may include an absorbing plate or layer 402 constructed of a light absorbing material, to absorb stray interfering light reflected from the egg and other components of the egg identification system 100 having reflective surfaces. The light controlling assembly 400 may be positioned between the emitter assemblies 200 and the detector assemblies 300, as shown in FIGS. 9, 20, 22 and 23. The light controlling assembly 400 may be coupled to a frame 162 of the egg identification device 160 for positioning between the emitter-detector pairs. In some instances, the light controlling assembly 400 may be coupled or attached to an upper frame plate 164. However, in other instances, the light controlling assembly 400 may be directly coupled to the frame 162 without the use of the upper frame plate 164.

The absorbing layer 402 defines one or more windows or openings 404 that allow light to pass therethrough to the egg, as shown in FIGS. 10-23. The absorbing layer 402 is used to absorb light reflected from the egg and other reflective surfaces during emission from the emitter assembly 200, thus reducing the interfering signal detectable by the detector assembly 300. That is, the light controlling assembly 400 reduces the interfering signal that does not carry information about the viability of the egg by capturing and dissipating such stray light. The absorbing layer 402 may have an opening or window pattern matching the egg pattern on an egg flat 50 such that it does not absorb light emitted from an emitter assembly 200 directly above the opening 404. In some instances, as shown in FIGS. 6, 7, 18, 19 and 23, the light controlling assembly 400 may be segmented into segments 425, which allow for various spacing configurations of the openings 404 to accommodate various egg flat 50 patterns. As a particular example shown in FIG. 19, the segments 425 may be offset to correspond with the offset spacing of the pockets 56 of the egg flat 50. The segments 425 allow for flexibility in constructing the light controlling assembly 400.

In some instances, the absorbing layer 402 may be a plate of material. In other instances, the absorbing layer 402 may be a coating applied to another material(s). According to some aspects, the absorbing layer 402 may be a multi-layer composite of anti-reflective coatings to provide destructive interference.

Positioning the absorbing layer 402 proximate to the emitter assembly 200 may reduce the need for a shroud or shielding around the egg identification device 160 or each individual egg during detection. In this regard, the light controlling assembly 400 provides advantages in that an improved output signal carrying embryo viability information may be achieved without the need for shielding to block ambient light, although such shielding could be provided for various reasons and purposes.

The absorbing layer 402 may be constructed of any material capable of absorbing light within a range of wavelengths to provide a desired rate of absorption. That is, the absorbing material may be chosen based on the wavelength(s) of the emitted electromagnetic radiation such that the reflected electromagnetic radiation is absorbed by the absorbing material. In some instances, it may be desirable to absorb greater than about 90% of the reflected stray light from the egg (and other reflective surfaces) at the desired wavelength, and preferably greater than about 95% of the reflected stray light, and most preferably greater than about 99% of the reflected stray light. In this regard, the absorbing layer 402 may have an internal transmittance of less than about 0.5, or preferably less than 0.1, or more preferably less than about 0.001, or most preferably less than about 0.0001 at the predetermined wavelength so as to absorb electromagnetic radiation at the predetermined wavelength. For a plate of material, the ratio of the flux leaving the entry surface to that reaching the exit surface is the internal transmittance. The internal transmittance describes the transmittance of the absorbing material without considering reflection losses.

According to one example, the emitter assembly 200 may emit electromagnetic radiation at a wavelength of between about 800 and about 1000 nanometers. In such instances, the absorbing layer 402 may be constructed out of an optical acrylic material or an optical glass material such as BG-39 (an ionically colored glass), BG-42 (an ionically colored glass), or S-8022 (an ionically colored glass) available from Schott AG, where the internal transmittance at such wavelengths is less than or about 1E-5. In some instances, multiple emitter assemblies may be used such that the absorbing layer 402 should be chosen so as to provide desired absorption at both wavelengths. For example, the BG-39, BG-42, or S-8022 materials may be used for a two emitter system emitting at 808 and 904 towards a single egg.

In some instances, a carbon matrix material or stained glass material may be used as the absorbing layer 402.

FIG. 24 is a graph illustrating internal transmittance as a function of wavelength for BG-39 optical glass material having a thickness of one millimeter. As shown, the internal transmittance is less than 1E-4 from the range of 800 nanometers to 1000 nanometers, thus providing a suitable material for the absorbing layer 402 when emitting light having a wavelength in the range of between about 800 and 1000 nanometers.

By reducing the amount of interfering signal detectable by the detector assembly 300, collection and analysis of the desired signal with information related to viability of the embryo may be improved. The thickness of the absorbing layer 402 may be adjusted or customized to provide the desired absorption characteristics at the predetermined wavelength. In the example above, the thickness of the absorbing layer 402 (BG-39) may be about 3 millimeters or more.

According to some aspects, the light controlling assembly 400 may include one or more anti-reflective coatings 410 applied to the absorbing layer 402, as shown in FIG. 12. In some instances, the anti-reflective coatings may be applied as multiple alternating layers of contrasting reflective index or as a graded index anti-reflective coating. The anti-reflective coating may be a hard glass material, such as $SiO_2$ or $MgF_2$ to provide scratch resistance that allows for cleaning of the light controlling assembly 400. The anti-reflective coating may provide at least <0.5% reflection at the surface for the predetermined wavelength range at incident angles of about 0-10 degrees. The anti-reflective coating may be chosen based on the wavelength(s) of the emitted electromagnetic radiation such that less than about 1% reflection is achieved. In some instances, materials such as $MgF_2$, $CeF_3$, $ZrO_2$, $Al_2O_3$ may be used to form multiple coating layers designed such that reflections from the surfaces undergo maximum destructive interference that may provide less than about 0.5% reflection.

According to some aspects of the present disclosure, as shown in FIGS. 13-20, 22 and 23, the light controlling assembly may include a transmitting layer 450 to provide protection to the emitter assembly 200. That is, the assembly may be constructed such that the emitting portions of the emitter assembly 200 are covered by the transmitting layer 450 so as to provide protection thereto from egg debris or other airborne debris. The transmitting layer 450 may be configured to allow transmission therethrough of electromagnetic radiation at the predetermined wavelength such that the electromagnetic radiation is able to reach the egg at a desired optical power. In some instances, the transmitting layer 450 may be provided in the form of plugs or discs 452 shaped to fit within the openings 404 of the absorbing layer 402, as shown in FIGS. 13-15 and 23, and attached thereto using appropriate fasteners such as, for example, an adhesive. In other instances, the transmitting layer 450 may be a plate or planar structure extending over the absorbing layer 402 to cover the openings 404, as shown in FIGS. 16, 17, 20 and 22, and coupled to the absorbing layer 402 using appropriate fasteners such as, for example, an adhesive. In instances where the transmitting layer 450 and the absorbing layer 402 are coupled using an adhesive, the adhesive may be optically matching to reduce interface reflection such that light is transmitted through the adhesive to the absorbing layer 402. That is, the adhesive may be chosen to minimize light reflection from the interface between the transmitting and absorbing layer materials. For example, Norland Optical Adhesives sold by Norland Products, Inc. may be used in such applications where a matching index of refraction is chosen as based on the absorbing and transmitting layer materials.

The transmitting layer 450 may be formed of any material capable of transmitting light within a range of wavelengths to provide a desired rate of transmittance. That is, the transmitting material may be chosen based on the wavelength(s) of the emitted electromagnetic radiation such that the reflected electromagnetic radiation is transmitted through the transmitting material such that it reaches the absorbing layer 402. In some instances, it may be desirable to transmit greater than about 90% of the emitted light from the emitter assembly 200 at the desired wavelength, and preferably greater than about 95%, and more preferably greater than about 99%, and most preferably greater than about 99.5%. In this regard, the transmitting layer 450 may have an internal transmittance of more than about 0.99, or preferably more than about 0.995, at the predetermined wavelength so as to transmit electromagnetic radiation therethrough at the predetermined wavelength.

For example, the emitter assembly 200 may emit electromagnetic radiation at a wavelength of between about 800 and about 1000 nanometers. In such instances, the transmitting layer 450 may be constructed out of an optical glass material such as, for example, borosilicate crown glass or N-BK 7 available from Schott AG, where the internal transmittance at such wavelengths is about 0.995 or greater. In some instances, multiple emitter assemblies may be used such that the transmitting layer 450 should be chosen so as to provide desired transmittance at multiple wavelengths. For example, the N-BK 7 material may be used for a two emitter system emitting at 808 and 904 towards a single egg.

According to some aspects, the light controlling assembly 400 may include one or more anti-reflective coatings 410 applied to the transmitting layer 450, as shown in FIGS. 15, 17, 20, 22 and 23, and as previously described with respect to the absorbing layer 402. In such an instance, the anti-reflective coating 410 may not be applied to the absorbing layer 402, but instead to the transmitting layer 450 only on the side opposite the absorbing layer 402 such that the anti-reflective coating 410 faces the egg 1. The thickness of the transmitting layer 450 may be adjusted or customized to provide the desired transmitted characteristics at the predetermined wavelength. In the example above, the thickness of the transmitting layer 450 (N-BK 7) may be between about 3 millimeters and about 6 millimeters.

As shown in FIGS. 20-23, according to some aspects, the detector assembly 300 may also or alternatively include a light controlling assembly 400 positioned proximately thereto for reducing detection of stray light and interfering signals. Such a setup may include the absorbing layer 402 with openings 404 defined to align with a detector window 320 such that light can be received within the detector assembly 300. The detector assembly 300 may include lenses 330, filters and/or other optical components for collecting the desired signal transmitted through the egg. As shown in FIG. 20, a light funnel 325 may be provided for improving detection of the light transmitted through an egg 1. In some instances, the light controlling assembly may include the transmitting layer 450 and one or more anti-reflective coatings 410 on the absorbing layer 402 or the transmitting layer 450 (if used). In some instances, the light controlling assembly 400 may be coupled or attached to the lower frame plate 166. However, in other instances, the light controlling assembly 400 may be directly coupled to the frame 162 or detector assembly 300 without the use of the lower frame plate 166.

FIGS. 25 and 26 are graphs illustrating the reduction in detectable stray signals when implementing a light controlling assembly 400 of various materials and configurations. That is, the graphs provide an absorption characteristic comparison of various light controlling assemblies 400 against a setup not using the light controlling assembly 400. To collect the data, a laser source was mounted to a plate having various light controlling assemblies 400 interchangeably mounted therebeneath. The thickness of the light controlling assembly 400 varied based on the composite layered structure thereof. The laser source emitted light at 808 nanometers toward an egg sitting upright on a light blocking pedestal (mechanical seal) positioned on a light diffuser plate configured to allow reflected light to pass therethrough such that it could be detected by a sensor (CCD camera) placed therebeneath. The absorbing layer 402 and the transmitting layer 450, when provided, were each 3 millimeters in thickness. An image was captured by the sensor at a one second exposure and then a software program was used to draw and collect linear data in two directions (perpendicular; one along the horizontal (FIG. 25) and one along the vertical (FIG. 26)) from the captured image. The y-axis is the relative sensor reading plotted in log scale and the x-axis is the pixel distance along the respective line. As shown, bare aluminum material (2) used in conventional systems provides an interfering signal about an order of magnitude higher than the various light controlling assemblies 400 (infrared absorbing coating on aluminum (3), BG-39 with near infrared anti-reflective (NIR-AR) coating (4), BG-39 with near infrared anti-reflective (NIR-AR) coating (5), and BG-39/N-BK 7 layered composite with anti-reflective coating (6)).

Many modifications and other aspects of the present disclosure set forth herein will come to mind to one skilled in the art to which this disclosure pertains having the benefit of the teachings presented in the foregoing descriptions and the associated drawings. For example, deflector cones and other shapes may be used to minimize top-plate reflections into the egg as an effective strategy for minimizing stray light. Therefore, it is to be understood that the present disclosure is not to be limited to the specific aspects disclosed and that modifications and other aspects are intended to be included within the scope of the appended claims. Although specific terms are employed herein, they are used in a generic and descriptive sense only and not for purposes of limitation.

That which is claimed:

1. An egg identification system for determining viability of an avian egg, comprising:
   an emitter assembly configured to emit electromagnetic radiation toward an egg, the electromagnetic radiation having a predetermined wavelength;
   a detector assembly spaced-apart from the emitter assembly and configured to detect electromagnetic radiation transmitted through the egg;
   a light controlling assembly positioned proximate to the emitter assembly and disposed between the emitter assembly and the detector assembly, the light controlling assembly comprising:
      an absorbing layer having an internal transmittance at the predetermined wavelength so as to be configured to absorb greater than about ninety percent of reflected electromagnetic radiation at the predetermined wavelength, the absorbing layer defining an opening through which electromagnetic radiation emitted from the emitter assembly is capable of passing therethrough toward the egg; and a transmitting layer configured to transmit therethrough electromagnetic radiation at the predetermined wavelength, the transmitting layer being operably engaged with the absorbing layer at the opening such that electromagnetic radiation emitted from the emitter assembly is transmitted through the transmitting layer, wherein the transmitting layer is in the form of a plug configured to fit within the opening defined by the absorbing layer; and a processor configured to process an output signal of the detector assembly to determine viability of the egg.

2. An egg identification system according to claim 1, wherein the light controlling assembly further comprises an anti-reflective coating applied to the absorbing layer.

3. An egg identification system according to claim 1, wherein the transmitting layer is operably engaged with the absorbing layer on a side opposite of the emitter assembly such that the absorbing layer is disposed between the emitter assembly and the transmitting layer and extends across the opening.

4. An egg identification system according to claim 3, further comprising an adhesive for bonding the absorbing layer to the transmitting layer, the adhesive being configured to optically match with the absorbing and transmitting layers such that electromagnetic radiation is transmitted at such formed interface.

5. An egg identification system according to claim 1, wherein the transmitting layer has an internal transmittance so as to be configured to transmit greater than about ninety percent of electromagnetic radiation from the emitter assembly at the predetermined wavelength.

6. An egg identification system according to claim 1, wherein the predetermined wavelength is between about 800 nanometers and 1000 nanometers.

7. An egg identification system according to claim 1, wherein the light controlling assembly further comprises an anti-reflective coating applied to the transmitting layer.

8. An egg identification system according to claim 1, wherein the absorbing and transmitting layers are formed of optical glass materials.

9. A method of determining viability of an egg, the method comprising:

emitting electromagnetic radiation from an emitter assembly at a predetermined wavelength, the electromagnetic radiation being emitted through an opening defined by an absorbing layer of a light controlling assembly and toward an egg, the absorbing layer having an internal transmittance at the predetermined wavelength so as to be configured to absorb greater than about ninety percent of reflected electromagnetic radiation at the predetermined wavelength;

transmitting electromagnetic radiation through a transmitting layer at the predetermined wavelength, the transmitting layer being operably engaged with the absorbing layer at the opening such that electromagnetic radiation emitted from the emitter assembly is transmitted through the transmitting layer, wherein the transmitting layer is in the form of a plug configured to fit within the opening defined by the absorbing layer;

absorbing, via the absorbing layer, electromagnetic radiation reflected from the egg and other reflective surfaces;

detecting electromagnetic radiation transmitted through the egg with a detector assembly spaced-apart from the emitter assembly;

generating an output signal from the electromagnetic radiation detected by the detector assembly; and processing the output signal to determine viability of the egg.

10. A method according to claim 9, wherein the electromagnetic radiation is transmitted through the transmitting layer at a rate greater than about ninety percent at the predetermined wavelength.

11. A method according to claim 9, wherein emitting electromagnetic radiation from an emitter assembly at a predetermined wavelength comprises emitting electromagnetic radiation having a wavelength of between about 800 nanometers and 1000 nanometers.

12. A method according to claim 9, wherein the absorbing layer and the transmitting layer are bonded together with an optically matching adhesive.

\* \* \* \* \*